United States Patent
Voloshin-Sela

(10) Patent No.: US 11,850,421 B2
(45) Date of Patent: Dec. 26, 2023

(54) COMPOSITIONS AND METHODS OF APPLYING ALTERNATING ELECTRIC FIELDS TO PLURIPOTENT STEM CELLS

(71) Applicant: NOVOCURE GMBH, Root (CH)

(72) Inventor: Tali Voloshin-Sela, Haifa (IL)

(73) Assignee: NOVOCURE GMBH, Root (CH)

( * ) Notice: Subject to any disclaimer, the term of this patent is extended or adjusted under 35 U.S.C. 154(b) by 0 days.

(21) Appl. No.: 17/314,659

(22) Filed: May 7, 2021

(65) Prior Publication Data

US 2021/0346691 A1 Nov. 11, 2021

Related U.S. Application Data

(60) Provisional application No. 63/022,162, filed on May 8, 2020.

(51) Int. Cl.
*A61N 1/36* (2006.01)
*A61N 1/04* (2006.01)

(52) U.S. Cl.
CPC ........... *A61N 1/36* (2013.01); *A61N 1/36002* (2017.08); *A61N 1/0476* (2013.01)

(58) Field of Classification Search
None
See application file for complete search history.

(56) References Cited

U.S. PATENT DOCUMENTS

| | | | |
|---|---|---|---|
| 6,261,286 B1 * | 7/2001 | Goble | A61B 18/14 606/34 |
| 2005/0090732 A1 | 4/2005 | Ivkov | |
| 2008/0097471 A1 * | 4/2008 | Adams | A61B 17/12136 606/119 |
| 2012/0283726 A1 | 11/2012 | Palti | |
| 2016/0045728 A1 * | 2/2016 | Lockwood | A61N 1/0521 607/39 |
| 2017/0281934 A1 * | 10/2017 | Giladi | A61N 1/32 |

FOREIGN PATENT DOCUMENTS

| TW | 110116837 | 5/2021 |
|---|---|---|
| WO | WO 2019/071261 | 4/2019 |
| WO | PCT/IB2021/000322 | 5/2021 |

OTHER PUBLICATIONS

Wikipedia, "Embryonic stem cell," accessed Jul. 27, 2022, https://en.wikipedia.org/wiki/Embryonic_stem_cell. (Year: 2022).*
Skubisz, M., Dutton, P., Duncan, W.C. et al. Using a decline in serum hCG between days 0-4 to predict ectopic pregnancy treatment success after single-dose methotrexate: a retrospective cohort study. BMC Pregnancy Childbirth 13, 30 (2013). https://doi.org/10.1186/1471-2393-13-30 (Year: 2013).*
Search Report and Written Opinion dated Sep. 15, 2021 by the International Searching Authority for PCT Application No. PCT/IB2021/000322, filed on May 7, 2021 (Applicant-Novocure GMBH) (17 pages).
U.S. Appl. No. 63/022,162, filed May 8, 2020, Voloshin-Sela.

* cited by examiner

*Primary Examiner* — Michael W Kahelin
(74) *Attorney, Agent, or Firm* — Ballard Spahr LLP

(57) ABSTRACT

Disclosed are methods and compositions for preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy.

10 Claims, 10 Drawing Sheets

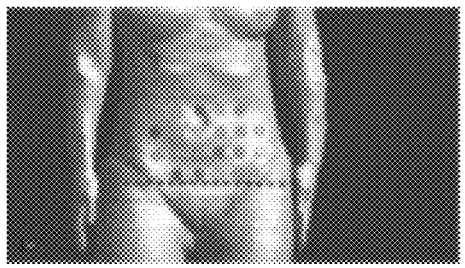
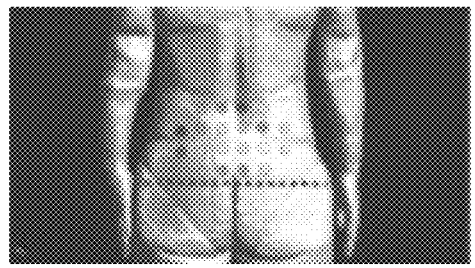
FIG. 5A  FIG. 5B
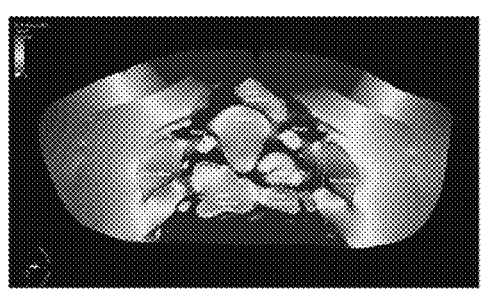
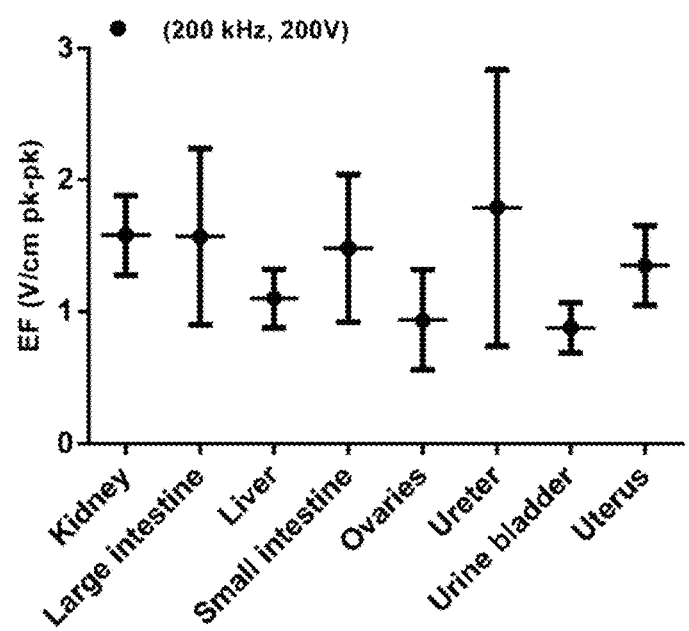
FIG. 5C  FIG. 5D

| Frequency (kHz) | Voltage (V pk-pk) | Organ | EF (V/cm pk-pk) |
|---|---|---|---|
| 200 | 200 | Kidney | 1.58±0.30 |
| | | Large intestine | 1.57±0.67 |
| | | Liver | 1.1±0.22 |
| | | Small intestine | 1.48±0.56 |
| | | Ovaries | 0.94±0.38 |
| | | Ureter | 1.79±1.05 |
| | | Urine bladder | 0.88±0.19 |
| | | Uterus | 1.35±0.30 |

FIG. 7

COMPOSITIONS AND METHODS OF APPLYING ALTERNATING ELECTRIC FIELDS TO PLURIPOTENT STEM CELLS

CROSS-REFERENCE TO RELATED APPLICATIONS

This application claims the benefit of U.S. Provisional Patent Application No. 63/022,162, filed on May 8, 2020, which is incorporated by reference herein in its entirety.

BACKGROUND

Tumor Treating Fields, or TTFields, are typically low intensity (e.g., 1-3 V/cm) alternating electric fields within the intermediate frequency range (100-300 kHz). TTFields can deliver alternating electric fields through non-invasive transducer arrays across the anatomical region of a tumor. TTFields have been established as an anti-mitotic cancer treatment modality because they interfere with proper micro-tubule assembly during metaphase and eventually destroy the cancerous cells during telophase, cytokinesis, or subsequent interphase. TTFields have been shown to not affect the viability of non-dividing normal cells, nerves, and muscles because of their low intensity. TTFields therapy is an approved mono-treatment for recurrent glioblastoma, and an approved combination therapy with chemotherapy for newly diagnosed glioblastoma and unresectable malignant pleural mesothelioma patients. These electric fields are induced non-invasively by transducer arrays (i.e., arrays of electrodes) placed directly on the patient's scalp in the case of treatment of glioblastoma, and on the patient's torso in the case of the treatment of pleural mesothelioma. TTFields also appear to be beneficial for treating tumors in other parts of the body.

The use of TTFields in regenerative medicine has been previously described in PCT/US19/57716. In part, PCT/US19/57716 describes methods of using TTFields to prevent teratoma formation in stem cell-based therapies by, in part, exposing a batch of differentiated progeny cells and residual pluripotent stem cells to an alternating electric field for a period of time that results in the death of pluripotent stem cells.

Pluripotent stem cells, including embryonic stem cells (ESCs or ES cells) and induced pluripotent stem cells (iPSCs or iPS cells), are a leading candidate for cell-based therapies because of their capacity for unlimited self-renewal and their ability to differentiate into any cell type in the body, including whatever cell type is needed to replace tissue that is damaged by disease or injury.

Prior to the filing of PCT/US19/57716, several attempts were made to selectively remove residual pluripotent stem cells from the pre-transplanted cells while sparing their differentiated progeny cells. These methods include the use of cytotoxic antibodies (Tan et al., 2009; Choo et al., 2008), specific antibody cell sorting (Tang et al., 2011; Fong et al., 2009), genetic manipulations including introduction of suicide genes (Blum et al., 2009; Schuldiner et al., 2003), pharmacological approaches (Lee et al., 2013; Ben-David et al. 2013; Lin et al., 2017), and radiation therapy (Lee et al., 2017). However, each of these methods has significant disadvantages, such high cost (cytotoxic antibodies and specific antibody cell sorting), variation among different lots (cytotoxic antibodies and specific antibody cell sorting), non-specific binding (cytotoxic antibodies), requirement of genetic manipulation and stable integration of toxic genes (genetic manipulation), time-consuming procedures (genetic manipulation, specific antibody cell sorting and cytotoxic antibodies), and use of ionizing radiation (radiation therapy).

There are several sources of stem cells such as bone marrow, umbilical cord, peripheral blood, germ cells and embryo/fetus tissues. Fetal stem cells (FSCs) and embryonic stem cells have been described as the most potent stem cell source.

The ability to control the growth of pluripotent stem cells or to eliminate pluripotent stem cells in sites of unwanted growth or cellular development presents a unique way to address otherwise uncontrolled pluripotent stem cell development and proliferation. For example, the ability to control pluripotent stem cell growth could assist in the management and treatment of disorders like cancer or ectopic pregnancies.

BRIEF SUMMARY

Disclosed are methods of preventing or disrupting mitosis of pluripotent stem cells comprising: exposing the pluripotent stem cells to an alternating electric field for a period of time, the alternating electric field having a frequency and field strength, wherein the frequency and field strength of the alternating electric field prevents or disrupts mitosis of the pluripotent stem cells.

Disclosed are methods of killing pluripotent stem cells comprising: exposing the pluripotent stem cells to an alternating electric field for a period of time, the alternating electric field having a frequency and field strength, wherein the frequency and field strength of the alternating electric field kills the pluripotent stem cells.

Disclosed are methods of preventing or disrupting division of pluripotent stem cells comprising: exposing the pluripotent stem cells to an alternating electric field for a period of time, the alternating electric field having a frequency and field strength, wherein the frequency and field strength of the alternating electric field prevents or disrupts division of the pluripotent stem cells.

Disclosed are methods of reducing the viability of pluripotent stem cells comprising: exposing the pluripotent stem cells to an alternating electric field for a period of time, the alternating electric field having a frequency and field strength, wherein the frequency and field strength of the alternating electric field reduces the viability of the pluripotent stem cells.

Disclosed are methods of slowing the progression or differentiation of pluripotent stem cell progression or differentiation in a subject comprising: exposing the pluripotent stem cell to an alternating electric field for a period of time, the alternating electric field having a frequency and field strength, wherein the frequency and field strength of the alternating electric field slows the progression of the pluripotent stem cell progression or differentiation in the subject.

Disclosed are methods of treating an ectopic pregnancy in a subject comprising: applying an alternating electric field to a target site of the subject for a period of time, the alternating electric field having a frequency and field strength, wherein the target site comprises an ectopic pregnancy.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIGS. 5A-D show distribution of TTFields within and in the vicinity of ovaries. Presentation of (FIG. 5A) anterior and (FIG. 5B) posterior field generating transducers. Dashed line signifies the level at which the axial slice (FIG. 5C) is depicted. (FIG. 5C) Field distribution simulation. Darker red areas represent adipose and muscle tissues. (FIG. 5D) Summary of organ specific distribution of TTFields intensity. Electric fields (EF) values were calculated using three dimensional modeling.

FIG. 7 shows examples of frequency, voltage and EF ranges that can be used in the disclosed methods and systems disclosed herein for particular organs.

DETAILED DESCRIPTION

Figure 1A:
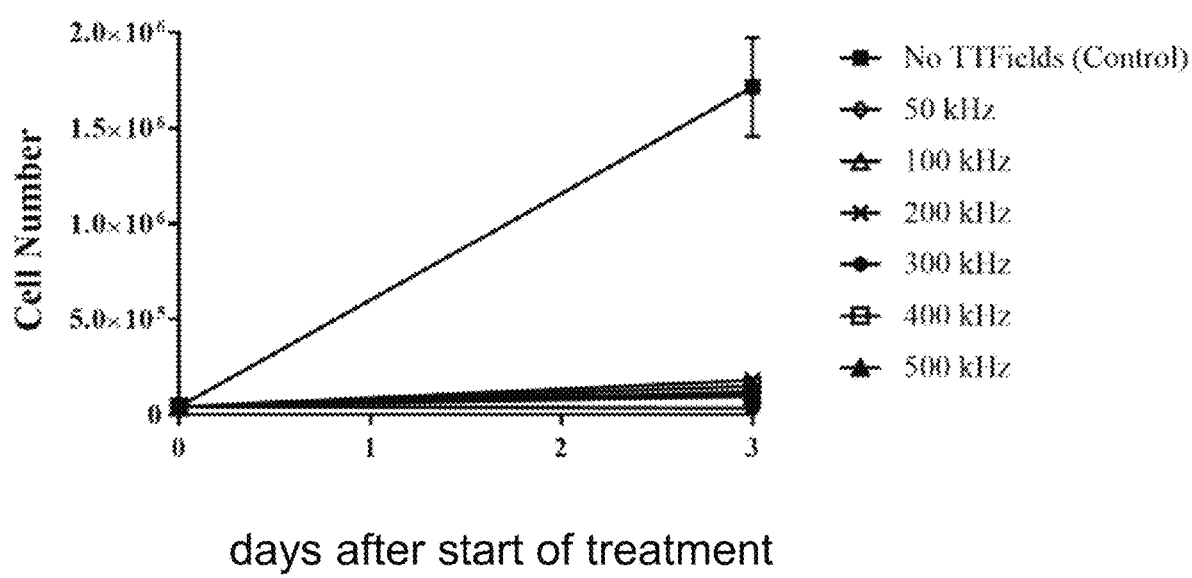
FIG. 1A depicts cell number counts as assessed by Trypan blue cell staining of the H7 human embryonic stem cells (H7-ESCs) that were exposed to alternating electric fields at different frequencies over time and compared to the non-exposed controls.
Figure 1B:
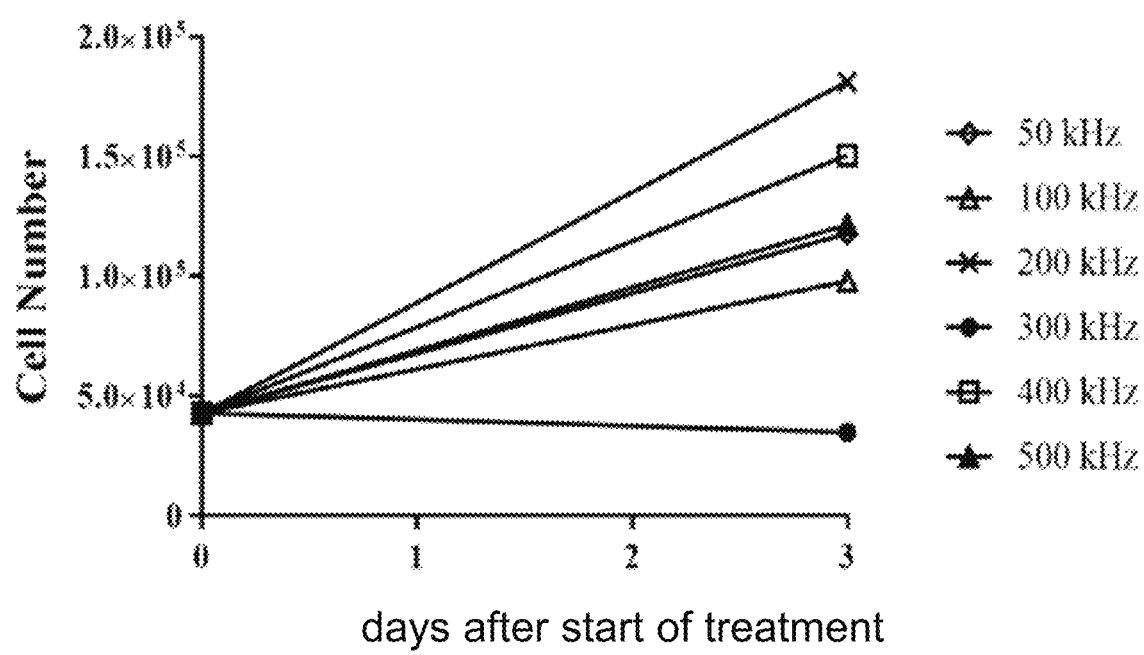
FIG. 1B is a zoomed-in version of the data shown in FIG. 1A of the H7-ESCs that were exposed to the alternating electric fields at the different frequencies over time.
Figure 2:
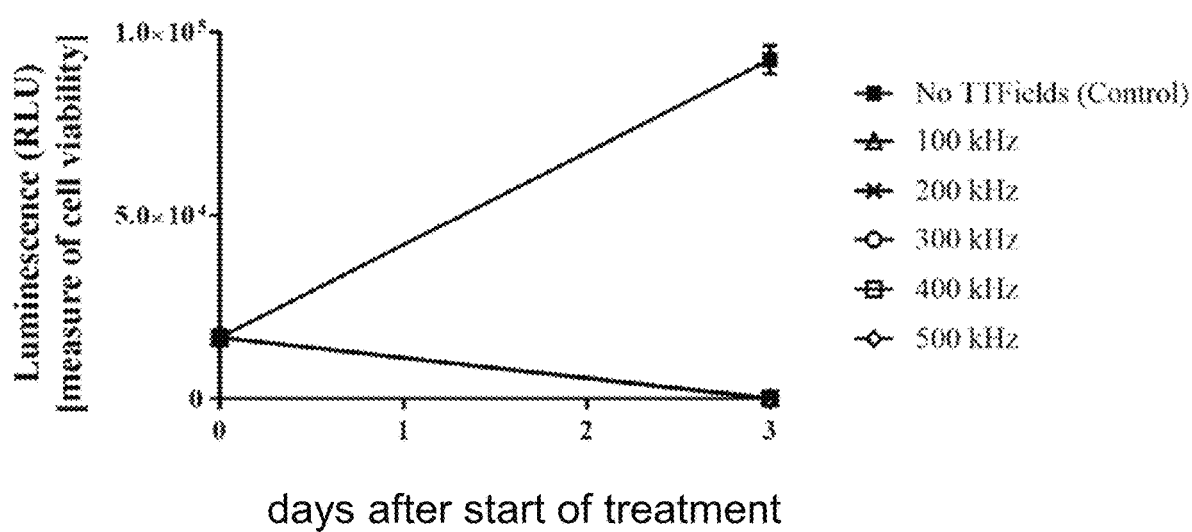
FIG. 2 depicts the cell viability of human ESCs (H7 line) over time when exposed to the alternating electric fields at the different frequencies and compared to the non-exposed controls. The luminescent output was positively correlated to the cell number ($R2=0.942$). RLU stands for relative luminescence unit.
Figure 3:
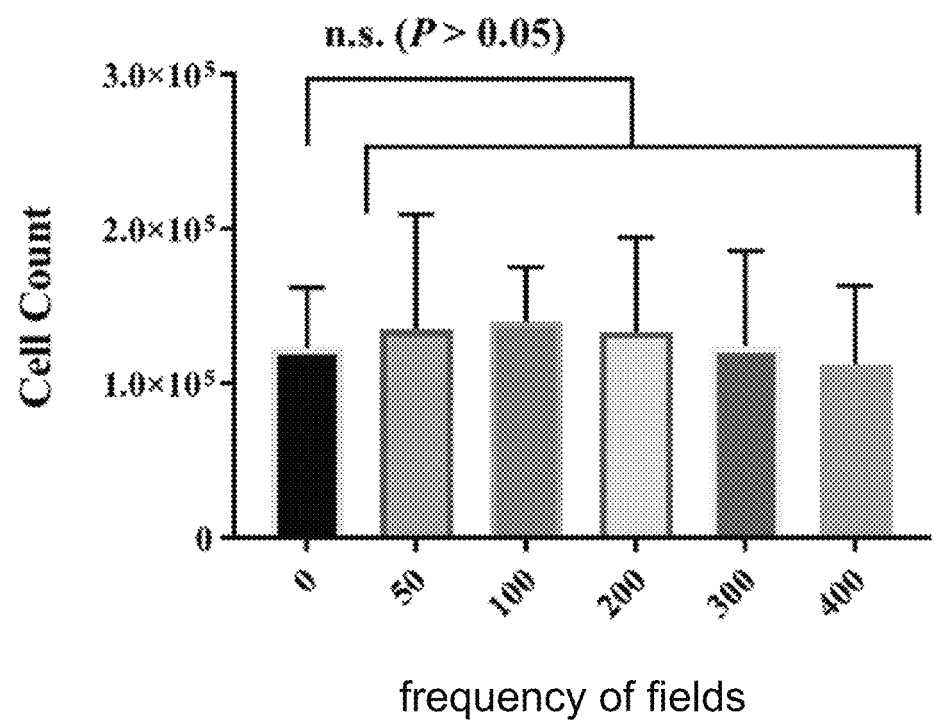
FIG. 3 depicts cell counts as assessed by Trypan blue cell staining of ESC-derived cardiomyocytes (ESC-CMs) after exposure to the alternating electric fields at the different frequencies and compared to the non-exposed control cardiomyocytes. There was no significant difference in the cardiomyocyte counts before and after the application of the alternating electric fields for any of the five frequencies that were tested.
Figure 4A:
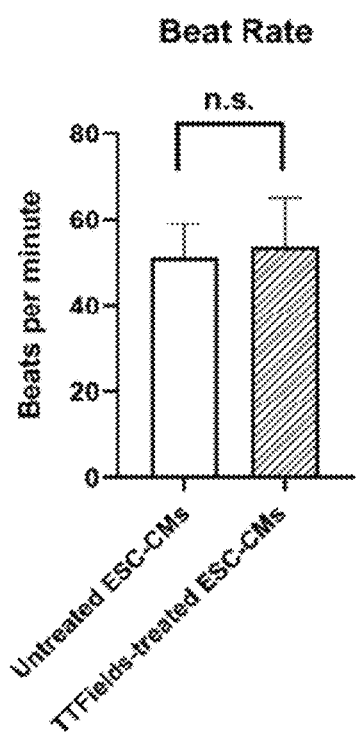
FIG. 4A depicts the results of a contractility assay that measured the beat rate of ESC-derived cardiomyocytes after exposure to the alternating electric fields and compared to the non-exposed (untreated) controls. The beat rate did not significantly differ between the ESC-CMs that were exposed to the alternating electric fields and those that were not exposed.
Figure 4B:
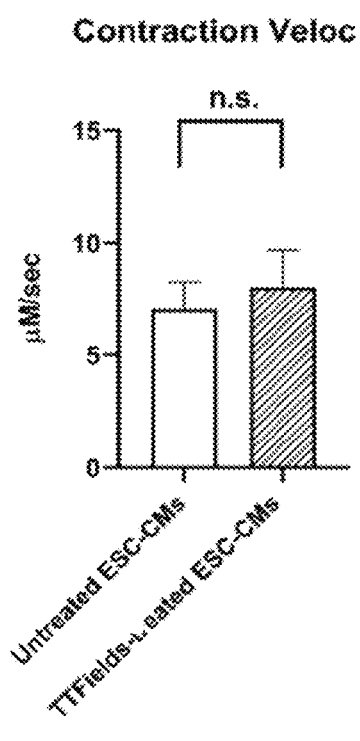
FIG. 4B depicts the results of a contractility assay that measured the contraction velocity of ESC-derived cardiomyocytes after exposure to the alternating electric fields and compared to the non-exposed (untreated) controls. The contraction velocity did not significantly differ between the ESC-CMs that were exposed to the alternating electric fields and those that were not exposed.
Figure 4C:
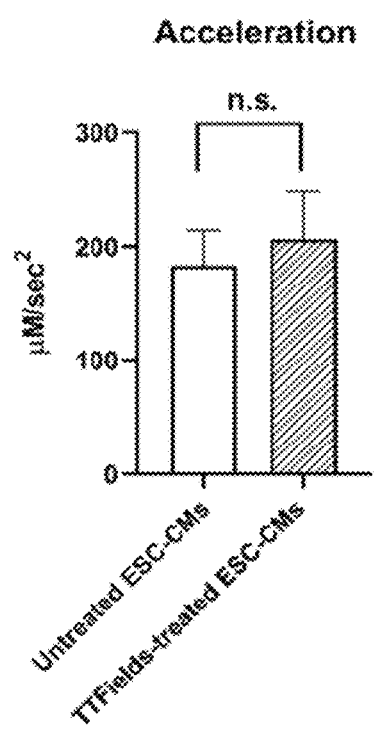
FIG. 4C depicts the results of a contractility assay that measured the acceleration of ESC-derived cardiomyocytes after exposure to the alternating electric fields and compared to the non-exposed (untreated) controls. The acceleration did not significantly differ between the ESC-CMs that were exposed to the alternating electric fields and those that were not exposed.

The disclosed method and compositions may be understood more readily by reference to the following detailed description of particular embodiments and the Examples included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C—F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. DEFINITIONS

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention, which will be limited only by the appended claims.

It must be noted that as used herein and in the appended claims, the singular forms "a", "an", and "the" include plural reference unless the context clearly dictates otherwise. Thus, for example, reference to "a nanoparticle" includes a single or a plurality of such nanoparticles, reference to "the nanoparticle" is a reference to one or more nanoparticles and equivalents thereof known to those skilled in the art, and so forth.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "comprising" can include the aspects "consisting of" and "consisting essentially of."

By "specifically binds," it is meant that an antibody or antibody fragment thereof recognizes and physically interacts with its cognate antigen (for example, a stem cell marker) and does not significantly recognize and interact with other antigens; such an antibody may be a polyclonal antibody or a monoclonal antibody, which are generated by techniques that are well known in the art.

By "probe," "primer," or oligonucleotide, it is meant a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for a stem cell marker can have at least 80%-90% sequence complementarity, preferably at least 91%-95% sequence complementarity, more preferably at least 96%-99% sequence complementarity, and most preferably 100% sequence complementarity to the stem cell marker to which they hybridize. Probes, primers, and oligonucleotides may be detectably-labeled, either radioactively, or non-radioactively, by methods well-known to those skilled in the art. Probes, primers, and oligonucleotides are used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, or electrophoretic mobility shift assay (EMSA).

By "specifically hybridizes," it is meant that a probe, primer, or oligonucleotide recognizes and physically interacts (that is, base-pairs) with a substantially complementary nucleic acid (for example, a stem cell marker) under high stringency conditions, and does not substantially base pair with other nucleic acids.

By "high stringency conditions," it is meant conditions that allow hybridization comparable with that resulting from the use of a DNA probe of at least 40 nucleotides in length, in a buffer containing 0.5 M NaHPO$_4$, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. (See, for example, F. Ausubel et al., Current Protocols in Molecular Biology, John Wiley & Sons, New York, NY, 1998). The term "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

As used herein, a "target site" is a specific site or location within or present on a subject or patient. For example, a "target site" can refer to, but is not limited to a cell (e.g., a pluripotent stem cell), a population of cells (e.g., a population of pluripotent stem cells), an organ, or tissue (e.g., uterine tissue or fallopian tissue). In some aspects, organs include, but are not limited to, lung, brain, pancreas, abdominal organs (e.g., stomach, intestine), ovary, breast, uterus, fallopian tube, cervix, prostate, bladder, liver, colon, or kidney. In some aspects, a cell or population of cells include, but are not limited to, pluripotent stem cells (e.g., embryonic or fetal stem cells), lung cells, brain cells, pancreatic cells, abdominal cells, ovarian cells, liver cells, colon cells, or kidney cells. In some aspects, a "target site" can be one or more pluripotent stem cells. In some aspects, a "target site" can be one or more pluripotent stem cells in or on a cesarean scar, fallopian tube, uterus, abdominal cavity, or cervix of a subject.

A "stem cell target site" is a site or location within or present on a subject or patient that comprises or is adjacent to one or more pluripotent stem cells, previously comprised one or more pluripotent stem cells, or is suspected of comprising one or more pluripotent stem cells. For example, a stem cell target site can refer to a site or location within or present on a subject or patient that is prone to pluripotent stem cell attachment or division.

As used herein, an "alternating electric field" or "alternating electric fields" refers to a very-low-intensity, directional, intermediate-frequency alternating electrical fields delivered to a subject, a sample obtained from a subject or to a specific location within a subject or patient (e.g., a target site or a stem cell target site). In some aspects, the alternating electric field can be in a single direction or multiple directional.

An example of an alternating electric field includes, but is not limited to, a Tumor Treating Field. In some aspects, TTFields can be delivered through two pairs of transducer arrays that generate perpendicular fields within the treated tumor. For example, for the Optune™ system (a TTFields delivery system), one pair of electrodes is located to the left and right (LR) of the tumor, and the other pair of electrodes is located anterior and posterior (AP) to a target site. Cycling the field between these two directions (i.e., LR and AP) ensures that a maximal range of cell orientations is targeted.

As described herein, TTFields have been established as an anti-mitotic cancer treatment modality because they interfere with proper micro-tubule assembly during metaphase and eventually destroy the cells during telophase, cytokinesis, or subsequent interphase. TTFields target solid tumors are described in U.S. Pat. No. 7,565,205, which is incorporated herein by reference in its entirety for its teaching of TTFields. As provided here, TTFields and alternating electric fields can also interfere with proper micro-tubule assembly during metaphase and eventually destroy pluripotent stem cells during telophase, cytokinesis, or subsequent interphase.

In vivo and in vitro studies show that the efficacy of alternating electric fields increases as the intensity of the electrical field increases. Therefore, optimizing array placement on a subject to increase the intensity in a target site is standard practice for the Optune system. Array placement optimization may be performed by "rule of thumb" (e.g., placing the arrays on the scalp as close to the tumor as possible), measurements describing the geometry of the patient's head, torsos or other body sites or body parts, tumor or target site dimensions, and/or tumor or stem cell location. Measurements used as input may be derived from imaging data. Imaging data is intended to include any type of visual data, such as for example, ultrasound, single-photon emission computed tomography (SPECT) image data, x-ray computed tomography (x-ray CT) data, magnetic resonance imaging (MRI) data, positron emission tomography (PET) data, data that can be captured by an optical instrument (e.g., a photographic camera, a charge-coupled device (CCD) camera, an infrared camera, etc.), and the like. In certain implementations, image data may include 3D data obtained from or generated by a 3D scanner (e.g., point cloud data). Optimization can rely on an understanding of how the electrical field distributes within the head, torso, or other body sites or body parts as a function of the positions of the array and, in some aspects, take account for variations in the electrical property distributions within the heads, torsos or other body sites or body parts of different patients.

The term "subject" refers to the target of administration, e.g. an animal. Thus, the subject of the disclosed methods can be a vertebrate, such as a mammal. For example, the subject can be a human. The term does not denote a particular age or sex. Subject can be used interchangeably with "individual" or "patient." For example, the target of administration can mean the recipient of the alternating electric field.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed methods and compositions belong. Although any methods and materials similar or equivalent to those described herein can be used in the practice or testing of the present methods and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinence of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. PLURIPOTENT STEM CELLS

Regenerative medicine is a game-changing area of medicine, which involves the process of creating living, functional tissues to repair or replace tissue or organ function lost due to age, disease, damage, or congenital defects. This field holds the promise of repairing or replacing damaged tissues and organs in the body by introducing outside cells, tissue, or even whole organs to integrate and become a part of tissues or replace whole organs. Importantly, regenerative medicine has the potential to solve the shortage of donor organs for patients who require life-saving organ transplantation.

One key to the success of regenerative medicine strategies has been the ability to isolate and generate stem cells, including pluripotent stem cells. Pluripotent stem cells, including embryonic stem cells (ESCs or ES cells) and induced pluripotent stem cells (iPSCs or iPS cells), are a leading candidate for cell-based therapies because of their capacity for unlimited self-renewal and their ability to differentiate into any cell type in the body, including whatever cell type is needed to replace tissue that is damaged by disease or injury.

By "pluripotency" and pluripotent stem cell, it is meant that such cells have the ability to undergo self-renewal and to differentiate into all types of cells in an organism. The definition of pluripotent stem cell is based on two properties: self-renewal and potency. The self-renewal is the capacity of the stem cells to divide indefinitely, producing unaltered cell daughters maintaining the same properties of the progenitor cell. In particular conditions or under specific signals, a stem cell is able to exit from self-renewal and engage a program leading to differentiation into specialized cell types deriving from the three germ layers (ectoderm, mesoderm, and endoderm).

There are different types of pluripotent stem cells including embryonic stem cells (ESCs), fetal stem cells (FSCs), and induced pluripotent stem cells (iPSCs). ESCs are derived from the inner cell mass (ICM) of preimplantation embryos and can be indefinitely maintained and expanded in the pluripotent state in vitro. Pluripotent stem cells can also be obtained by inducing dedifferentiation of adult somatic cells through a recently developed in vitro technology, known as cell reprogramming.

Similarly to ESCs, iPSCs can be expanded indefinitely and they are able to differentiate in all the derivatives of the three germ layers. The term "induced pluripotent stem cell" encompasses pluripotent cells, that, like embryonic stem cells, can be cultured over a long period of time while maintaining the ability to differentiate into all types of cells in an organism, but that, unlike ES cells (which are derived from the inner cell mass of blastocysts), are derived from differentiated somatic cells, that is, cells that had a narrower, more defined potential and that in the absence of experimental manipulation could not give rise to all types of cells in the organism. iPSCs have an ESC-like morphology, growing as flat colonies with large nucleo-cytoplasmic ratios, defined borders and prominent nuclei. In addition, iPSCs cells express one or more key pluripotency markers known by one of ordinary skill in the art, including but not limited to alkaline phosphatase, SSEA3, SSEA4, Sox2, Oct3/4, Nanog, TRA160, TRA181, TDGF 1, Dnmt3b, FoxD3, GDF3, Cyp26a1, TERT, and Zfp42. In addition, iPSCs are capable of forming teratomas. In addition, they are capable of forming or contributing to ectoderm, mesoderm, or endoderm tissues in a living organism.

C. NANOPARTICLES

Disclosed herein are methods involving nanoparticles. Any of the nanoparticles described herein can be used for one or more of the disclosed methods.

In some aspects, the nanoparticle can comprise a conducting or semi-conducting material. For example, the nanoparticle can comprise or consist of carbon gold, ferrous iron, selenium, silver, copper, platinum, iron oxide, graphene, iron dextran, superparamagnetic iron oxide, boron-doped detonation nanodiamonds, or a combination thereof. In some aspects, the nanoparticle can comprise an alloy selected from Au/Ag, Au/Cu, Au/Ag/Cu, Au/Pt, Au/Fe, Au/Cu or Au/Fe/Cu.

In some aspects, the nanoparticle can be a conductive nanoparticle. A conductive nanoparticle can increase conductivity and lower impedance in a target site or stem cell target site. Thus, in some aspects of the disclosed methods, the impedance in a target site or stem cell target site is lowered and/or the conductivity in a target site or stem cell target site is increased.

In some aspects, the nanoparticle can be a non-conductive nanoparticle. In some aspects, the non-conductive nanoparticle is a ferroelectric nanoparticle. Ferroelectric nanoparticles have emerged as promising tools for enhancing electric stimulation of cells and tissues. Several nanotransducers have been revealed to mediate photodynamic and magneto-thermal conversions, and to deliver locally anticancer stimuli to reduce tumor burden in the field of nanooncology. Cell and tissue penetration of these nanotransducers could be controlled by remote electrical stimulation. Among ferroelectric nanoparticles, barium titanate nanoparticles (BTNPs) have high dielectric constants and suitable piezoelectric characteristics with high biocompatibility. Such non-conductive nanoparticles can be used in the methods disclosed herein to be taken up by a cell via TTFields stimulation and to promote the action of TTFields by enhancing cell cycle-related apoptosis in a pluripotent stem cell. In some aspects, the non-conductive nanoparticle is not a ferroelectric nanoparticle. A non-conductive nanoparticle can decrease conductivity and increase impedance in a target site or stem cell target site. Thus, in some aspects of the disclosed methods, the impedance in a target site or stem cell target site is increased and/or the conductivity in a target site or stem cell target site is decreased.

In some aspects, a population of nanoparticles can be used in the methods disclosed herein. In some aspects, the population of nanoparticles can include conductive and non-conductive nanoparticles.

Nanoparticles (NPs) internalization into cells is known to be dependent on particle size and zeta potential. NPs under 200 nm can be engulfed by cancer cells through a clathrin-dependent pathway or a macro-pinocytosis pathway. In some aspects, the size of the nanoparticle can be between 0.5 nm and 100 nm. In some aspects, the size of the nanoparticle can be between 0.5 nm & 2.5 nm. In some aspects, the size of the nanoparticle can be between 100 nm and 200 nm. In some aspects, the size of the nanoparticle can be greater than 100 nm. In some aspects, the disclosed methods allow for the use of nanoparticles (e.g., metal/magnetic NPs), in a size range of 100 nm-200 nm (preferentially up to 150 nm to avoid accumulation in the liver and spleen), to target pluripotent stem cells in vivo.

In some aspects, the nanoparticle has a particular three-dimensional shape. For example, the nanoparticle can be a nanocube, nanotube, NanoBipyramid, NanoPlate, Nano-Cluster, Nanochaine, NanoStar, NanoShuttle, NanoHollow, dendrimer, nanorod, nanoshell, nanocage, nanosphere, nanofiber, or nanowire, or a combination thereof.

In some aspects, the nanoparticle can be mesoporous or nonporous.

In some aspects, the nanoparticle can be coated with a polysaccharide, poly amino acid, or synthetic polymer. Suitable coating for the nanoparticle can be chosen to decrease the toxicity of the nanoparticle and can provide the nanoparticle with the capacity for selective interaction with different types of cells and biological molecules. Suitable coating for the nanoparticle can be chosen to improve the nanoparticle biocompatibility and solubility in water and biological fluids by decreasing their aggregation capacity or increasing their stability. Suitable coating for the nanoparticle can be chosen to influence the nanoparticle pharmacokinetics, changing the, reactivity or patterns of the nanoparticle and/or distribution and accumulation in the body.

In some aspects, the nanoparticles can be incorporated into a scaffold prior to introducing the nanoparticles to the subject. In some aspects, the nanoparticles can be loaded onto or within a scaffold prior to or after introducing the scaffold to a subject. For example, a scaffold could be surgically provided to a subject and subsequently one or more of the nanoparticles described herein could be administered to the subject under conditions that allow for the nanoparticles to incorporate into the scaffold. Alternatively, nanoparticles could be incorporated into a scaffold outside of a subject and then the nanoparticle-loaded scaffold could be surgically provided to a subject.

Examples of scaffolds include, but are not limited to, scaffolds comprising natural polymers such as hyaluronic acid, fibrin, chitosan, and collagen. Examples of scaffolds include, but are not limited to scaffolds comprising synthetic polymers such as polyethylene glycol (PEG), polypropylene fumarate (PPF), polyanhydride, polycaprolactone (PCL), polyphosphazene, polyether ether ketone (PEEK), polylactic acid (PLA), and poly (glycolic acid) (PGA).

In some aspects, the nanoparticle is conjugated to one or more ligands. In some aspects, the one or more ligands can be conjugated to the nanoparticle via a linker. In some aspects, a linker comprises a thiol group, a C2 to C12 alkyl group, a C2 to C12 glycol group or a peptide. In some aspects, the linker comprises a thiol group represented by the general formula HO—(CH)n, —S—S— (CH2)m-OH wherein n and m are independently between 1 and 5. In some aspects, the one or more ligands are a small molecule, nucleic acid, carbohydrate, lipid, peptide, antibody, antibody fragment, or a therapeutic agent. For example the one or more ligands can be, but are not limited to, an anticancer drug, a cytotoxic drug, a pain-management drug, pseudomonas exotoxin A, a non-radioactive isotope (e.g., boron-10 for boron neutron capture therapy), or a photosensitizer (e.g., photofrin, foscan, 5-aminolevulinic acid, Mono-L-aspartyl chlorin e6, pthalocyanines, Meta-tetra (hydroxyphenyl) porphyrins, texaphyrins, or Tin ethyl etipurpurin).

In some aspects, nanoparticles can be targeted to the stem cell, pluripotent stem cell or stem cell target site using stem cell-targeting moieties. Stem cell-targeting moieties can be, but are not limited to, folate, transferrin, aptamers, antibodies, antibody fragments, nucleic acids and peptides. Thus, in some aspects, the nanoparticle can be introduced to the subject in a targeted or non-targeted manner.

In some aspects, the nanoparticle is conjugated to or coated with a stem cell marker. In some aspects, the stem cell marker can be SSEA-1, SSEA-3, SSEA-4, CD324 (E-Cadherin), CD90 (Thy-1), CD117 (c-KIT, SCFR), CD326, CD9 (MRP1, TM4SF DRAP-27, p24), CD29 ($\beta$1 integrin), CD24 (HAS), CD59 (Protectin), CD133, CD31 (PECAM-1), CD49f (Integrin a6/CD29), TRA-1-60, TRA-1-81 or Frizzled5.

In some aspects, the nanoparticle is conjugated to or coated with a peptide, antibody or antibody fragment that specifically binds or specifically hybridizes to a stem cell marker. In some aspects, the stem cell marker can be SSEA-1, SSEA-3, SSEA-4, CD324 (E-Cadherin), CD90 (Thy-1), CD117 (c-KIT, SCFR), CD326, CD9 (MRP1, TM4SF DRAP-27, p24), CD29 ($\beta$1 integrin), CD24 (HAS), CD59 (Protectin), CD133, CD31 (PECAM-1), CD49f (Integrin a6/CD29), TRA-1-60, TRA-1-81 or Frizzled5.

As used herein, the term "antibodies" is used in a broad sense and includes both polyclonal and monoclonal antibodies. In addition to intact immunoglobulin molecules, also disclosed are antibody fragments or polymers of those immunoglobulin molecules, and human or humanized versions of immunoglobulin molecules or fragments thereof, as long as they are chosen for their ability to interact with the polypeptides disclosed herein. "Antibody fragments" are portions of a complete antibody. A complete antibody refers to an antibody having two complete light chains and two complete heavy chains. An antibody fragment lacks all or a portion of one or more of the chains. Examples of antibody fragments include, but are not limited to, half antibodies and fragments of half antibodies. A half antibody is composed of a single light chain and a single heavy chain. Half antibodies and half antibody fragments can be produced by reducing an antibody or antibody fragment having two light chains and two heavy chains. Such antibody fragments are referred to as reduced antibodies. Reduced antibodies have exposed and reactive sulfhydryl groups. These sulfhydryl groups can be used as reactive chemical groups or coupling of biomolecules to the antibody fragment. A preferred half antibody fragment is a F(ab). The hinge region of an antibody or antibody fragment is the region where the light chain ends and the heavy chain goes on.

Antibody fragments for use in the methods disclosed herein can bind antigens (e.g., microbe-specific antibodies or one or more of the microbes described herein). Preferably, the antibody fragment can be specific for an antigen. An antibody or antibody fragment is specific for an antigen if it binds with significantly greater affinity to one epitope than to other epitopes. The antigen can be any molecule, compound, composition, or portion thereof to which an antibody fragment can bind. For example, the antigen can be a microbe-specific antibody or one or more of the microbes described herein. An analyte can be any molecule, compound or composition of interest. The antibodies or antibody fragments can be tested for their desired activity using the in vitro assays described herein, or by analogous methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. Also disclosed are "chimeric" antibodies in which a portion of the heavy or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity. (See, U.S. Pat. No. 4,816,567 and Morrison et al., Proc. Natl. Acad. Sci. USA, 81:6851 6855 (1984)).

Monoclonal antibodies can be made using any procedure that produces monoclonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent.

Monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, such as an Fv, Fab, Fab', or other antigen binding portion of an antibody, can be accomplished using routine techniques known in the art. For example, digestion can be performed using papain. Examples of papain digestion are described in WO 94/29348 published Dec. 22, 1994 and U.S. Pat. No. 4,342,566, the contents of which are hereby incorporated by reference in its entirety for its teaching of papain digestion of antibodies to prepare monovalent antibodies. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

Fragments, whether attached to other sequences, can also include insertions, deletions, substitutions, or other selected modifications of particular regions or specific amino acid residues, provided the activity of the antibody or antibody fragment is not significantly altered or impaired compared to the non-modified antibody or antibody fragment. These modifications can provide for some additional property, such as to remove/add amino acids capable of disulfide bonding, to increase bio-longevity, to alter secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Human antibodies can be prepared using any technique. Examples of techniques for human monoclonal antibody production include those described by Cole et al. (Monoclonal Antibodies and Cancer Therapy, Alan R. Liss, p. 77, 1985) and by Boerner et al. (J. Immunol., 147(1):86 95, 1991). Human antibodies (and fragments thereof) can also be produced using phage display libraries (Hoogenboom et al., J. Mol. Biol., 227:381, 1991; Marks et al., J. Mol. Biol., 222:581, 1991).

Human antibodies can also be obtained from transgenic animals. For example, transgenic, mutant mice that are capable of producing a full repertoire of human antibodies, in response to immunization, have been described. (See, e.g., Jakobovits et al., Proc. Natl. Acad. Sci. USA, 90:2551-255 (1993); Jakobovits et al., Nature, 362:255 258 (1993); Bruggermann et al., Year in Immunol., 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ line antibody gene array into such germ line mutant mice results in the production of human antibodies upon antigen challenge. Antibodies having the desired activity are selected using Env-CD4-co-receptor complexes as described herein.

Optionally, human antibodies can be made from memory B cells using a method for Epstein-Barr virus transformation of human B cells. (See, e.g., Triaggiai et al., An efficient method to make human monoclonal antibodies from memory B cells: potent neutralization of SARS coronavirus, Nat Med. 2004 August; 10(8):871-5. (2004)), which is herein incorporated by reference in its entirety for its teaching of a method to make human monoclonal antibodies from memory B cells). In short, memory B cells from a subject who has survived a natural infection are isolated and immortalized with EBV in the presence of irradiated mononuclear cells and a CpG oligonuleotide that acts as a polyclonal activator of memory B cells. The memory B cells are cultured and analyzed for the presence of specific antibodies. EBV-B cells from the culture producing the antibodies of the desired specificity are then cloned by limiting dilution in the presence of irradiated mononuclear cells, with the addition of CpG 2006 to increase cloning efficiency, and cultured. After culture of the EBV-B cells, monoclonal antibodies can be isolated. Such a method offers (1) antibodies that are produced by immortalization of memory B lymphocytes, which are stable over a lifetime and can easily be isolated from peripheral blood; and (2) the antibodies isolated from a primed natural host who has survived a natural infection, thus eliminating the need for immunization of experimental animals, which may show different susceptibility and, therefore, different immune responses.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen binding portion of an antibody), which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues that are found neither in the recipient antibody nor in the imported CDR or framework sequences. Generally, a humanized antibody has one or more amino acid residues introduced into it from a source that is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., Nature, 321:522-525 (1986), Reichmann et al., Nature, 332:323 327 (1988), and Presta, Curr. Opin. Struct. Biol., 2:593-596 (1992)).

Methods for humanizing non-human antibodies are well known in the art. For example, humanized antibodies can be generated according to the methods of Winter and co-workers (Jones et al., Nature, 321:522 525 (1986), Riechmann et al., Nature, 332:323-327 (1988), Verhoeyen et al., Science, 239:1534 1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.). The antibodies disclosed herein can also be administered to a subject. Nucleic acid approaches for antibody delivery also exist. The broadly neutralizing antibodies to the polypeptides disclosed herein and antibody fragments can also be administered to subjects or subjects as a nucleic acid preparation (e.g., DNA or RNA) that encodes the antibody or antibody fragment, such that the subject's own cells take up the nucleic acid and produce and secrete the encoded antibody or antibody fragment.

In some aspects, the nanoparticle can be a labeled nanoparticle. In some aspects, labeled nanoparticles can be magnetic nanoparticles, nanoparticles decorated with Gd3+, nanoparticles decorated with radioisotopes (e.g., technetium-99m, iodine-123, iodine-131, fluorine-18 carbon-11, nitrogen-13, oxygen-15, gallium-68, zirconium-89, and rubidium-82), nanoparticles decorated with a fluorescent label (e.g., Quantum dots), nanoparticles decorated with photosensitizer (e.g., photofrin, foscan, 5-aminolevulinic acid, Mono-L-aspartyl chlorin e6, pthalocyanines, Metatetra(hydroxyphenyl)porphyrins, texaphyrins, or Tin ethyl etipurpurin), or nanoparticles decorated with dye. In some aspects, the nanoparticle can be coated with a labeled antibody and therefore the nanoparticle is indirectly labeled. In some aspects, if there are size constraints, the nanoparticles, if decorated or conjugated to a large moiety, can be of a smaller size to accommodate a larger moiety.

Other examples of nanoparticles include, but are not limited to, silica nanoparticles, hydrophilic polymers (e.g., polyacrylamide (PAA), polyurethanes, poly(hydroxyethyl methacrylamide) (pHEMA), certain poly(ethylene glycols)), and hydrophobic polymers (e.g., polystyrene nanoparticles).

In some aspects, the nanoparticle can be introduced into a target site. In some aspects, the nanoparticle can be introduced into a stem cell target site. In some aspects, the nanoparticle can be introduced into a stem cell or pluripotent stem cell. In some aspects, the nanoparticle can be introduced into a location in a subject suspected of comprising one or more stem cells or pluripotent stem cells. In some aspects, the nanoparticle can be introduced into to a site or location within or present on a subject or patient that is prone to dividing or differentiating stem cells or pluripotent stem cells. In some aspects, the nanoparticle can be introduced into a site or location of dividing or differentiating stem cells or pluripotent stem cells within or present on a subject or patient. In some aspects, the nanoparticle can be introduced into the stem cell or pluripotent stem cell via injection. In some aspects, the nanoparticle can be introduced into a site adjacent to a target site. In some aspects, the nanoparticle can be introduced into a site adjacent to a location in a subject suspected of comprising one or more dividing or differentiating stem cells or pluripotent stem cells.

In some aspects, the nanoparticle can be introduced into a target site adjacent to a stem cell target site. In some aspects, the nanoparticle can be introduced into a stem cell target site, wherein the stem cell target site is adjacent to a stem cell or pluripotent stem cell. In some aspects, the nanoparticle can be introduced into a stem cell target site, wherein the stem cell target site is adjacent to a location in a subject suspected of comprising one or more stem cells. In some aspects, the nanoparticle can be introduced into a stem cell target site, wherein the stem cell target site is adjacent to a site or location within or present on a subject or patient that is prone to pluripotent stem cell mitosis, division, differentiation or progression. In some aspects, the nanoparticle can be introduced into a stem cell target site, wherein the stem cell target site is adjacent to a site or location of pluripotent stem cell mitosis, division, or progression within or present on a subject or patient. In some aspects, the nanoparticle can be introduced into a stem cell target site, wherein the stem cell target site is adjacent to the stem cell or pluripotent stem cell via injection. In some aspects, the nanoparticle can be introduced into a stem cell target site, wherein the stem cell target site is adjacent to the stem cell or pluripotent stem cell via intracellular injection (e.g., computed tomography-guided, during surgery or biopsy).

In some aspects, the nanoparticle can be introduced intratumorally, intracranially, intraventricularly, intrathecally, epidurally, intradurally, intravascularly, intravenously (targeted or non-targeted), intraarterially, intramuscularly, subcutaneously, intraperitoneally, orally, intranasally, via intracellular injection (e.g., computed tomography-guided, during surgery or biopsy) or via inhalation. In some aspects, nanoparticles can be targeted to the stem cell or stem cell target site using stem cell-targeting moieties. Stem cell-targeting moieties can be, but are not limited to, folate, transferrin, aptamers, antibodies, antibody fragments, nucleic acids and peptides. Thus, in some aspects, the nanoparticle can be introduced to the subject in a targeted or non-targeted manner.

In some aspects, the nanoparticle can be introduced at a concentration based on cell volume, method of delivery, limitations of the device administering the alternating electric field, patient weight, patient age, size of cell, the type of cell, location of the cells, age of the patient, or any other physical or genotypic attribute of the patient, stem cell or pluripotent stem cell. In some aspects, the size of the nanoparticles can be used to determine the concentration of the nanoparticles to be introduced. In some aspects, the nanoparticle can be introduced at about 0.001 to 0.01, 0.01 to 0.1, 0.1 to 0.5, 0.5 to 5, 5 to 10, 10 to 20, 20 to 50, 50 to 100, 100 to 200, 200 to 300, 300 to 400, 400 to 500, 500 to 600, 600 to 700, 700 to 800, 800 to 900, or 900 to 1000 ng per $mm^3$ of stem cells or pluripotent stem cells. In some aspects, the nanoparticle can be introduced at about 0.001 to 0.01, 0.01 to 0.1, 0.1 to 0.5, 0.5 to 5, 5 to 10, 10 to 20, 20 to 50, 50 to 100, 100 to 200, 200 to 300, 300 to 400, 400 to 500, 500 to 600, 600 to 700, 700 to 800, 800 to 900, or 900 to 1000 µg.

In some aspects, the nanoparticle can be introduced to the subject once, twice, or three or more times.

D. PHARMACEUTICAL COMPOSITIONS

Disclosed herein are pharmaceutical compositions comprising one or more of the nanoparticles described herein. In some aspects, the nanoparticles described herein can be provided in a pharmaceutical composition. For example, the nanoparticles described herein can be formulated with a pharmaceutically acceptable carrier.

Disclosed herein are compositions comprising one or more of the nanoparticles described herein that further comprise a carrier such as a pharmaceutically acceptable carrier. For example, disclosed are pharmaceutical compositions, comprising the nanoparticles disclosed herein, and a pharmaceutically acceptable carrier.

For example, the nanoparticles described herein can comprise a pharmaceutically acceptable carrier. By "pharmaceutically acceptable," it is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy (19th ed.) ed. A. R. Gennaro, Mack Publishing Company, Easton, PA 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of nanoparticle being administered. These most typically would be standard carriers for administration of drugs to humans, including solutions such as sterile water, saline, and buffered solutions at physiological pH.

Pharmaceutical compositions can also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

In the methods described herein, delivery (or administration or introduction) of the nanoparticles or pharmaceutical compositions disclosed herein to subjects can be via a variety of mechanisms.

E. METHOD OF PREVENTING OR DISRUPTING MITOSIS OF PLURIPOTENT STEM CELLS

As described herein, the ability to control the growth of pluripotent stem cells or to eliminate pluripotent stem cells in sites of unwanted growth or cellular development presents a unique way to address otherwise uncontrolled pluripotent stem cell development and proliferation. For example, the ability to control pluripotent stem cell growth could assists in the management and treatment of disorders like cancer or ectopic pregnancies.

In women, fertilization typically occurs in the fallopian tubes, while the distinction between the inner cell mass (ICM) and the trophectoderm (TE) (Yamanaka et al., 2006), and the switch from totipotency to pluripotency typically takes place during embryogenesis in the uterus (Surani et al., 2007). In most pregnancies, embryonic development during the pregnancy occurs in the uterus of the woman. An ectopic pregnancy denotes a pregnancy occurring elsewhere than in the cavity of the uterus. In humans, it accounts for approximately 1-2% of all pregnancies (approximately 100,000 per year in the United States and 10,000 per year in the United Kingdom). When an ectopic pregnancy occurs in the fallopian tube, the cellular processes of embryonic development may continue inside the fallopian tube until clinical intervention. An ectopic pregnancy can cause the fallopian tube to burst open. Without treatment, the ruptured tube can lead to life-threatening bleeding. If the tube has become stretched or has ruptured and started bleeding, part or all of it may have to be removed. In this case, bleeding needs to be stopped promptly, and emergency surgery is necessary.

The pathology of an ectopic pregnancy has been recognized and often results in numerous maternal deaths during the first trimester of pregnancy. There are several classifications of an ectopic pregnancy including (i) tubal pregnancy; (ii) nontubal ectopic pregnancy; (iii) heterotropic pregnancy; and (iv) persistent ectopic pregnancy. A tubal pregnancy occurs when an oocyte is fertilized and then remains in the fallopian tube. A nontubal ectopic pregnancy occurs in the ovary, cervix, or an intra-abdominal space, and accounts for approximately 2% of all ectopic pregnancies. In rare cases of ectopic pregnancy, there may be two fertilized eggs, one outside the uterus and the other inside, which is referred to as a heterotropic pregnancy. A persistent ectopic pregnancy refers to the continuation of trophoblastic growth after a surgical intervention to remove an ectopic pregnancy. In certain situations, the embryo could problematically embed itself on a caesarean section scar.

Treatment for ectopic pregnancies can be harsh and invasive. Early treatment of an ectopic pregnancy with methotrexate is a viable alternative to surgical treatment. If administered early in the pregnancy, methotrexate terminates the growth of the developing embryo; the embryo may then be either resorbed by the woman's body or pass with a menstrual period. Contraindications for methotrexate treatment of an ectopic pregnancy include liver, kidney, or blood disease, as well as an ectopic embryonic mass greater than 3.5 cm. Also, treatment with methotrexate may lead to the inadvertent termination of an undetected intrauterine pregnancy, or severe abnormality in any surviving embryo. Therefore, it is recommended that methotrexate should only be administered when hCG has been serially monitored with a rise less than 35% over 48 hours, which practically excludes a viable intrauterine pregnancy.

If bleeding due to an ectopic pregnancy has already occurred, surgical intervention may be necessary. However, whether to pursue surgical intervention is an often difficult decision in a stable patient with minimal evidence of blood clot on ultrasound.

The compositions, systems and methods disclosed herein can overcome many of the challenges currently faced in treating ectopic pregnancies, by relying on less invasive methods of using TTFields. The compositions, systems and methods disclosed herein can also be used when current standards of care and treatments are not available to the subject. For example, methotrexate sometimes is not a possibility for women with high blood pressure, who are taking blood-thinning medication for any other reason, or who are breastfeeding. Contraception should be used throughout and for three months after methotrexate treatment as it is teratogenic (which can be avoided when using TTFields). Methotrexate and its metabolites are known to cause birth defects and they stay in the body for period ranging from 1 to 12 months after treatment. Therefore at least a 3-6 month waiting period is recommended for women who are planning pregnancy after stopping methotrexate therapy (which also can be avoided when using TTFields). Additionally, there is a risk for toxicity following concurrent administration of methotrexate with: NSAIDs (i.e. Aspirin, Etodolac, Flurbiprofen, Ibuprofen, Ketoprofen, Naproxen, Sulindac), antibiotics (i.e. Trimethoprim, Cephalosporins, Ciprofloxacin, Doxycycline, Penicillin, Amoxicillin, Oxacillin, Piperacillin/tazobactam, Probenecid, Vancomycin), proton pump inhibitors (i.e. Omeprazole, Esomeprazole, Pantoprazole, Lansoprazole), Cyclosporine, or Vitamin C. The compositions, systems and methods disclosed herein can also be used to treat such patients and subjects.

Disclosed are methods of preventing or disrupting mitosis of pluripotent stem cells using TTFields. Disclosed are methods of preventing or disrupting mitosis of pluripotent stem cells comprising: exposing the pluripotent stem cells to an alternating electric field for a period of time, the alternating electric field having a frequency and field strength, wherein the frequency and field strength of the alternating electric field prevents or disrupts mitosis of the pluripotent stem cells. In some aspects, the pluripotent stem cells are fetal stem cells or embryonic stem cells.

As used herein, the terms "prevent mitosis" or "preventing mitosis" can refer to arresting the cell (e.g. pluripotent stem cells) at one or more of the phases of mitosis (prophase, prometaphase, metaphase, anaphase, or telophase). As used herein, the terms "disrupt mitosis" or "disrupting mitosis" can refer to altering or stalling the cell (e.g. pluripotent stem cells) at one or more of the phases of mitosis (prophase, prometaphase, metaphase, anaphase, or telophase). In some aspects, mitosis can be prevented or disrupted in the current or subsequent rounds or phases of mitosis of the cell. In some aspects, the pluripotent stem cells exposed to the alternating electric field undergo mitotic slippage. Mitotic slippage occurs when the cells arrested exit mitosis without dividing. When cells undergo mitotic slippage, they exit mitosis without undergoing cytokinesis, and become tetraploid. In cells that undergo mitotic slippage, the exposure to the alternating electric field can prevent further mitosis. In some aspects, preventing or disrupting in the current or subsequent rounds or phases of mitosis of the cell.

Disclosed are methods of preventing or disrupting mitosis of pluripotent stem cells in a target site of a subject, comprising applying an alternating electric field to the target site of the subject for a period of time, the alternating electric field having a frequency and field strength, wherein the frequency and field strength of the alternating electric field in the target site of the subject prevents or disrupts mitosis of the pluripotent stem cells in the target site. In some aspects, the target site is a stem cell target site. In some aspects, the pluripotent stem cells are fetal stem cells or embryonic stem cells. In some aspects, the target site a fallopian tube, uterus, abdominal cavity, or cervix of the subject.

Disclosed are methods of preventing or disrupting mitosis of pluripotent stem cells using TTFields, further comprising administering gefitinib, methotrexate, or a combination thereof to the subject. In some aspects, the methods of preventing or disrupting mitosis of pluripotent stem cells or methods of preventing or disrupting mitosis of pluripotent stem cells in a target site of a subject further comprises administering gefitinib, methotrexate, or a combination thereof to the subject. In some aspects of the methods of preventing or disrupting mitosis of pluripotent stem cells or methods of preventing or disrupting mitosis of pluripotent stem cells in a target site the subject is pregnant, has elevated levels of human chorionic gonadotropin (HCG), has been identified to have elevated levels of human chorionic gonadotropin (HCG), has been identified to have an abnormal pattern in the rise of levels of human chorionic gonadotropin (HCG), or has been diagnosed with an ectopic pregnancy, has been identified to have elevated levels of human chorionic gonadotropin (HCG), has been identified to have an abnormal pattern in the rise of levels of human chorionic gonadotropin (HCG), or has been identified or diagnosed via (transvaginal) ultrasound. In some aspects, subject has one or more of the following characteristics selected from the group consisting of: (i) a gestational sac size in the range of from about 0.5 cm to about 10 cm; and (ii) a β-hCG concentration in the range of from about 200 to about 100,000 IU/L. In some aspects, the gestational sac size is in the range of from about 1 cm to about 8 cm. In some aspects, the gestational sac size is in the range of from about 3 cm to about 6 cm. In some aspects, wherein the gestational sac size is in the range of from about 3 cm to about 5 cm.

In some aspects, the methods further comprise observation, laparoscopy, laparotomy, or medication. In some aspects, the methods further comprise administering gefitinib, methotrexate, or a combination thereof to the subject.

Disclosed are methods of preventing or disrupting mitosis of pluripotent stem cells comprising: exposing the pluripotent stem cells to an alternating electric field for a period of time, the alternating electric field having a frequency and field strength, wherein the frequency and field strength of the alternating electric field prevents or disrupts mitosis of the pluripotent stem cells, wherein the method further comprises altering the electric impedance of the alternating electric field. Disclosed are methods of preventing or disrupting mitosis of pluripotent stem cells comprising: exposing the pluripotent stem cells to an alternating electric field for a period of time, the alternating electric field having a frequency and field strength, wherein the frequency and field strength of the alternating electric field prevents or disrupts mitosis of the pluripotent stem cells, wherein the method further comprises altering the electric impedance of the alternating electric field in a site adjacent to the pluripotent stem cells, comprising: introducing a non-conductive nanoparticle to a site adjacent to the pluripotent stem cells in the subject; and applying an alternating electric field to the site adjacent to the pluripotent stem cells of the subject, wherein the electric impedance in the site of the pluripotent stem cells adjacent to the alternating electric field is altered.

F. METHOD OF KILLING OF PLURIPOTENT STEM CELLS

Disclosed are methods of killing pluripotent stem cells using TTFields. Disclosed are methods of killing pluripotent stem cells comprising: exposing the pluripotent stem cells to an alternating electric field for a period of time, the alternating electric field having a frequency and field strength, wherein the frequency and field strength of the alternating electric field kills the pluripotent stem cells. In some aspects, the pluripotent stem cells are fetal stem cells or embryonic stem cells.

Disclosed are methods of killing pluripotent stem cells in a target site of a subject, comprising applying an alternating electric field to the target site of the subject for a period of time, the alternating electric field having a frequency and field strength, wherein the frequency and field strength of the alternating electric field in the target site of the subject kills the pluripotent stem cells in the target site. In some aspects, the target site is a stem cell target site. In some aspects, the pluripotent stem cells are fetal stem cells or embryonic stem cells. In some aspects, the target site is a fallopian tube, uterus, abdominal cavity, or cervix of the subject.

Disclosed are methods of killing pluripotent stem cells using TTFields, further comprising administering gefitinib, methotrexate, or a combination thereof to the subject. In some aspects, the methods of killing pluripotent stem cells or methods of killing pluripotent stem cells in a target site of a subject further comprises administering gefitinib, methotrexate, or a combination thereof to the subject. In some aspects of the methods of killing pluripotent stem cells or methods of killing pluripotent stem cells in a target site the subject is pregnant, has elevated levels of human chorionic gonadotropin (HCG), has been identified to have elevated levels of human chorionic gonadotropin (HCG), has been identified to have an abnormal pattern in the rise of levels of human chorionic gonadotropin (HCG), or has been diagnosed with an ectopic pregnancy, has been identified to have elevated levels of human chorionic gonadotropin (HCG), has been identified to have an abnormal pattern in the rise of levels of human chorionic gonadotropin (HCG), or has been identified or diagnosed via (transvaginal) ultrasound. In some aspects, subject has one or more of the following characteristics selected from the group consisting of: (i) a gestational sac size in the range of from about 0.5 cm to about 10 cm; and (ii) a β-hCG concentration in the range of from about 200 to about 100,000 IU/L. In some aspects, the gestational sac size is in the range of from about 1 cm to about 8 cm. In some aspects, the gestational sac size is in the range of from about 3 cm to about 6 cm. In some aspects, wherein the gestational sac size is in the range of from about 3 cm to about 5 cm.

In some aspects, the methods further comprise observation, laparoscopy, laparotomy, or medication. In some aspects, the methods further comprise administering gefitinib, methotrexate, or a combination thereof to the subject.

Disclosed are methods of killing pluripotent stem cells comprising: exposing the pluripotent stem cells to an alternating electric field for a period of time, the alternating electric field having a frequency and field strength, wherein the frequency and field strength of the alternating electric field kills the pluripotent stem cells, wherein the method further comprises altering the electric impedance of the alternating electric field in a site adjacent to the pluripotent stem cells, comprising: introducing a non-conductive nanoparticle to a site adjacent to the pluripotent stem cells in the subject; and applying an alternating electric field to the site adjacent to the pluripotent stem cells of the subject, wherein the electric impedance in the site of the pluripotent stem cells adjacent to the alternating electric field is altered.

G. METHOD OF PREVENTING OR DISRUPTING DIVISION OF PLURIPOTENT STEM CELLS

Disclosed are methods of preventing or disrupting division of pluripotent stem cells using TTFields. Disclosed are methods of preventing or disrupting division of pluripotent stem cells comprising: exposing the pluripotent stem cells to an alternating electric field for a period of time, the alternating electric field having a frequency and field strength, wherein the frequency and field strength of the alternating electric field prevents or disrupts division of the pluripotent stem cells. In some aspects, the pluripotent stem cells are fetal stem cells or embryonic stem cells.

Disclosed are methods of preventing or disrupting division of pluripotent stem cells in a target site of a subject, comprising applying an alternating electric field to the target site of the subject for a period of time, the alternating electric field having a frequency and field strength, wherein the frequency and field strength of the alternating electric field in the target site of the subject prevents or disrupts division of the pluripotent stem cells in the target site. In some aspects, the target site is a stem cell target site. In some aspects, the pluripotent stem cells are fetal stem cells or embryonic stem cells. In some aspects, the target site is a fallopian tube, uterus, abdominal cavity, or cervix of the subject.

Disclosed are methods of preventing or disrupting division of pluripotent stem cells using TTFields, further comprising administering gefitinib, methotrexate, or a combination thereof to the subject. In some aspects, the methods of preventing or disrupting division of pluripotent stem cells or methods of preventing or disrupting division of pluripotent stem cells in a target site of a subject further comprises administering gefitinib, methotrexate, or a combination thereof to the subject. In some aspects of the methods of preventing or disrupting division of pluripotent stem cells or methods of preventing or disrupting division of pluripotent stem cells in a target site the subject is pregnant, has elevated levels of human chorionic gonadotropin (HCG), has been identified to have elevated levels of human chorionic gonadotropin (HCG), has been identified to have an abnormal pattern in the rise of levels of human chorionic gonadotropin (HCG), or has been diagnosed with an ectopic pregnancy, has been identified to have elevated levels of human chorionic gonadotropin (HCG), has been identified to have an abnormal pattern in the rise of levels of human chorionic gonadotropin (HCG), or has been identified or diagnosed via (transvaginal) ultrasound. In some aspects, subject has one or more of the following characteristics selected from the group consisting of: (i) a gestational sac size in the range of from about 0.5 cm to about 10 cm; and (ii) a β-hCG concentration in the range of from about 200 to about 100,000 IU/L. In some aspects, the gestational sac size is in the range of from about 1 cm to about 8 cm. In some aspects, the gestational sac size is in the range of from about 3 cm to about 6 cm. In some aspects, wherein the gestational sac size is in the range of from about 3 cm to about 5 cm.

In some aspects, the methods further comprise observation, laparoscopy, laparotomy, or medication. In some aspects, the methods further comprise administering gefitinib, methotrexate, or a combination thereof to the subject.

Disclosed are methods of preventing or disrupting division of pluripotent stem cells comprising: exposing the pluripotent stem cells to an alternating electric field for a period of time, the alternating electric field having a frequency and field strength, wherein the frequency and field strength of the alternating electric field prevents or disrupts division of the pluripotent stem cells, wherein the method further comprises altering the electric impedance of the alternating electric field in a site adjacent to the pluripotent stem cells, comprising: introducing a non-conductive nanoparticle to a site adjacent to the pluripotent stem cells in the subject; and applying an alternating electric field to the site adjacent to the pluripotent stem cells of the subject, wherein the electric impedance in the site of the pluripotent stem cells adjacent to the alternating electric field is altered.

H. METHOD OF REDUCING VIABILITY OF PLURIPOTENT STEM CELLS

Disclosed are methods of reducing the viability of pluripotent stem cells using TTFields. Disclosed are methods of reducing the viability of pluripotent stem cells comprising: exposing the pluripotent stem cells to an alternating electric field for a period of time, the alternating electric field having a frequency and field strength, wherein the frequency and field strength of the alternating electric field reduces the viability of the pluripotent stem cells. In some aspects, the pluripotent stem cells are fetal stem cells or embryonic stem cells.

Disclosed are methods of reducing the viability of pluripotent stem cells in a target site of a subject, comprising applying an alternating electric field to the target site of the subject for a period of time, the alternating electric field having a frequency and field strength, wherein the frequency and field strength of the alternating electric field in the target site of the subject reduces the viability of the pluripotent stem cells in the target site. In some aspects, the target site is a stem cell target site. In some aspects, the pluripotent stem cells are fetal stem cells or embryonic stem cells. In some aspects, the target site is a fallopian tube, uterus, abdominal cavity, or cervix of the subject.

Disclosed are methods of reducing the viability of pluripotent stem cells using TTFields, further comprising administering gefitinib, methotrexate, or a combination thereof to the subject. In some aspects, the methods of reducing the viability of pluripotent stem cells or methods of reducing the viability of pluripotent stem cells in a target site of a subject further comprises administering gefitinib, methotrexate, or a combination thereof to the subject. In some aspects of the methods of reducing the viability of pluripotent stem cells or methods of reducing the viability of pluripotent stem cells in a target site the subject is pregnant, has elevated levels of human chorionic gonadotropin (HCG), has been identified to have elevated levels of human chorionic gonadotropin (HCG), has been identified to have an abnormal pattern in the rise of levels of human chorionic gonadotropin (HCG), or has been diagnosed with an ectopic pregnancy, has been identified to have elevated levels of human chorionic gonadotropin (HCG), has been identified to have an abnormal pattern in the rise of levels of human chorionic gonadotropin (HCG), or has been identified or diagnosed via (transvaginal) ultrasound. In some aspects, subject has one or more of the following characteristics selected from the group consisting of: (i) a gestational sac size in the range of from about 0.5 cm to about 10 cm; and (ii) a β-hCG concentration in the range of from about 200 to about 100,000 IU/L. In some aspects, the gestational sac size is in the range of from about 1 cm to about 8 cm. In some aspects, the gestational sac size is in the range of from about 3 cm to about 6 cm. In some aspects, wherein the gestational sac size is in the range of from about 3 cm to about 5 cm.

In some aspects, the methods further comprise observation, laparoscopy, laparotomy, or medication. In some aspects, the methods further comprise administering gefitinib, methotrexate, or a combination thereof to the subject.

Disclosed are methods of reducing the viability of pluripotent stem cells comprising: exposing the pluripotent stem cells to an alternating electric field for a period of time, the alternating electric field having a frequency and field strength, wherein the frequency and field strength of the alternating electric field reduces the viability of the pluripotent stem cells, wherein the method further comprises altering the electric impedance of the alternating electric field in a site adjacent to the pluripotent stem cells, comprising: introducing a non-conductive nanoparticle to a site adjacent to the pluripotent stem cells in the subject; and applying an alternating electric field to the site adjacent to the pluripotent stem cells of the subject, wherein the electric impedance in the site of the pluripotent stem cells adjacent to the alternating electric field is altered.

I. METHOD OF SLOWING THE PROGRESSION OF PLURIPOTENT STEM CELL PROGRESSION OR DIFFERENTIATION

Disclosed are methods of slowing the progression or differentiation of pluripotent stem cells using TTFields. Disclosed are methods of slowing the progression or differentiation of pluripotent stem cell progression or differentiation in a subject comprising: exposing the pluripotent stem cell to an alternating electric field for a period of time, the alternating electric field having a frequency and field strength, wherein the frequency and field strength of the alternating electric field slows the progression of the pluripotent stem cell progression or differentiation in the subject. In some aspects, the pluripotent stem cells are fetal stem cells or embryonic stem cells.

Disclosed are methods of slowing the progression or differentiation of pluripotent stem cells in a target site of a subject, comprising applying an alternating electric field to the target site of the subject for a period of time, the alternating electric field having a frequency and field strength, wherein the frequency and field strength of the alternating electric field in the target site of the subject slows the progression or differentiation of the pluripotent stem cells in the target site. In some aspects, the target site is a stem cell target site. In some aspects, the pluripotent stem cells are fetal stem cells or embryonic stem cells. In some aspects, the target site is a fallopian tube, uterus, abdominal cavity, or cervix of the subject.

Disclosed are methods of slowing the progression or differentiation of pluripotent stem cells using TTFields, further comprising administering gefitinib, methotrexate, or a combination thereof to the subject. In some aspects, the methods of slowing the progression or differentiation of pluripotent stem cells or methods of slowing the progression or differentiation of pluripotent stem cells in a target site of a subject further comprises administering gefitinib, methotrexate, or a combination thereof to the subject. In some aspects of the methods of slowing the progression or differentiation of pluripotent stem cells or methods of slowing the progression or differentiation of pluripotent stem cells in a target site the subject is pregnant, has elevated levels of human chorionic gonadotropin (HCG), has been identified to have elevated levels of human chorionic gonadotropin (HCG), has been identified to have an abnormal pattern in the rise of levels of human chorionic gonadotropin (HCG), or has been diagnosed with an ectopic pregnancy, has been identified to have elevated levels of human chorionic gonadotropin (HCG), has been identified to have an abnormal pattern in the rise of levels of human chorionic gonadotropin (HCG), or has been identified or diagnosed via (transvaginal) ultrasound. In some aspects, subject has one or more of the following characteristics selected from the group consisting of: (i) a gestational sac size in the range of from about 0.5 cm to about 10 cm; and (ii) a β-hCG concentration in the range of from about 200 to about 100,000 IU/L. In some aspects, the gestational sac size is in the range of from about 1 cm to about 8 cm. In some aspects, the gestational sac size is in the range of from about 3 cm to about 6 cm. In some aspects, wherein the gestational sac size is in the range of from about 3 cm to about 5 cm.

In some aspects, the methods further comprise observation, laparoscopy, laparotomy, or medication. In some aspects, the methods further comprise administering gefitinib, methotrexate, or a combination thereof to the subject.

Disclosed are methods of slowing the progression or differentiation of pluripotent stem cells comprising: exposing the pluripotent stem cells to an alternating electric field for a period of time, the alternating electric field having a frequency and field strength, wherein the frequency and field strength of the alternating electric field slows the progression or differentiation of the pluripotent stem cells, wherein the method further comprises altering the electric impedance of the alternating electric field in a site adjacent to the pluripotent stem cells, comprising: introducing a non-conductive nanoparticle to a site adjacent to the pluripotent stem cells in the subject; and applying an alternating electric field to the site adjacent to the pluripotent stem cells of the subject, wherein the electric impedance in the site of the pluripotent stem cells adjacent to the alternating electric field is altered.

J. METHOD OF TREATING ECTOPIC PREGNANCY

Disclosed are methods of treating an ectopic pregnancy in a subject using TTFields. Disclosed are methods of treating an ectopic pregnancy in a subject comprising: applying an alternating electric field to a target site of the subject for a period of time, the alternating electric field having a frequency and field strength, wherein the target site comprises an ectopic pregnancy. In some aspects, the target site is a stem cell target site. In some aspects, the target site is a fallopian tube, uterus, abdominal cavity, or cervix of the subject.

In some aspects of the methods of treating an ectopic pregnancy, the method further comprises the additional step of first diagnosing an ectopic pregnancy in the subject. In some aspects of the methods of treating an ectopic pregnancy, the subject is pregnant, has elevated levels of human chorionic gonadotropin (HCG), has been identified to have elevated levels of human chorionic gonadotropin (HCG), has been identified to have an abnormal pattern in the rise of levels of human chorionic gonadotropin (HCG), has been diagnosed with an ectopic pregnancy, has been identified to have elevated levels of human chorionic gonadotropin (HCG), has been identified to have an abnormal pattern in the rise of levels of human chorionic gonadotropin (HCG), or has been identified or diagnosed via (transvaginal) ultrasound. In some aspects of the methods of treating an ectopic pregnancy, the method further comprises the additional step of first diagnosing the subject as pregnant, having elevated levels of human chorionic gonadotropin (HCG), having elevated levels of human chorionic gonadotropin (HCG), having an abnormal pattern in the rise of levels of human chorionic gonadotropin (HCG), having been diagnosed with an ectopic pregnancy, having elevated levels of human chorionic gonadotropin (HCG), having an abnormal pattern in the rise of levels of human chorionic gonadotropin (HCG), or has been identified or diagnosed via (transvaginal) ultrasound. In some aspects, subject has one or more of the following characteristics selected from the group consisting of: (i) a gestational sac size in the range of from about 0.5 cm to about 10 cm; and (ii) a β-hCG concentration in the range of from about 200 to about 100,000 IU/L. In some aspects, the gestational sac size is in the range of from about 1 cm to about 8 cm. In some aspects, the gestational sac size is in the range of from about 3 cm to about 6 cm. In some aspects, wherein the gestational sac size is in the range of from about 3 cm to about 5 cm.

In some aspects, the methods further comprise observation, laparoscopy, laparotomy, or medication. In some aspects, the methods further comprise administering gefitinib, methotrexate, or a combination thereof to the subject.

K. ALTERING IMPEDANCE IN A TARGET SITE

The methods disclosed herein can further comprise altering the electrical impedance to an alternating electric field in a site adjacent to the pluripotent stem cells or target site of a subject. The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise altering the electric impedance to an alternating electric field in a site adjacent to the pluripotent stem cells or target site of the subject, comprising: introducing a non-conductive nanoparticle to a site adjacent to the target site in the subject; and applying an alternating electric field to the site adjacent to the pluripotent stem cells or target site of the subject, wherein the electric impedance in the site adjacent to the pluripotent stem cells or target site of the subject to the alternating current is altered.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise: introducing a non-conductive nanoparticle to a site adjacent to the pluripotent stem cells or target site of a subject; and applying an alternating electric field to the site adjacent to the pluripotent stem cells or target site of the subject, wherein the electric impedance in the site adjacent to the pluripotent stem cells or target site of the subject to the alternating current is altered, wherein the current density and/or power loss density in the site adjacent to the pluripotent stem cells or target site of the subject to the alternating current is altered. In some aspects, the conductivity is decreased in the site adjacent to the target site. In some aspects, the impedance in the site adjacent to the pluripotent stem cells or target site of the subject is increased. In some aspects, the conductivity is increased in the pluripotent stem cells or target site. In some aspects, the impedance in the pluripotent stem cells or target site is decreased. In some aspects, the non-conductive nanoparticle is not a ferroelectric nanoparticle.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise altering the electric impedance to an alternating electric field in a target site of a subject, comprising: introducing a conductive nanoparticle to a target site in the subject, and applying an alternating electric field to the target site of the subject, wherein the electric impedance in the target site of the subject to the alternating current is altered.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise altering the electric impedance to an alternating electric field in a target site of a subject, comprising: introducing a conductive nanoparticle to a target site in the subject; and applying an alternating electric field to the target site of the subject, wherein the electric impedance in the target site of the subject to the alternating current is altered, wherein the current density and/or power loss density in the target site of the subject to the alternating current is altered, wherein the impedance in the target site is lowered and/or wherein the conductivity in the target site is increased.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise altering the electric impedance to an alternating electric field in a target site of a subject, comprising: introducing a conductive nanoparticle to a target site in the subject; and applying an alternating electric field to the target site of the subject, wherein the electric impedance in the target site of the subject to the alternating current is altered, wherein the current density and/or power loss density in the target site of the subject to the alternating current is altered, wherein the method further comprises introducing a non-conductive nanoparticle to a site adjacent to the target site in the subject; and applying an alternating electric field to the site adjacent to the target site of the subject. In some aspects, the current density and/or power loss density in the target site of the subject to the alternating current is altered. In some aspects, the conductivity is decreased in the site adjacent to the target site. In some aspects, the impedance in the site adjacent to the target site is increased. In some aspects, the conductivity is increased in the target site. In some aspects, the impedance in the target site is decreased.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise methods of altering the electric impedance to an alternating electric field in a target site of a subject, comprising: introducing a conductive nanoparticle to a target site in the subject; and applying an alternating electric field to the target site of the subject, wherein the electric impedance in the target site of the subject to the alternating current is altered, wherein the current density and/or power loss density in the target site of the subject to the alternating current is altered, wherein the non-conductive nanoparticle is not a ferroelectric nanoparticle. In some aspects, the impedance in the target site is increased and/or the conductivity in the target site is decreased.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise methods of altering the electric impedance to an alternating electric field in a target site of a subject, comprising: introducing a conductive nanoparticle to a target site in the subject; and applying an alternating electric field to the target site of the subject, wherein the electric impedance in the target site of the subject to the alternating current is altered, wherein the current density and/or power loss density in the target site of the subject to the alternating current is altered, wherein the alternating electric field is a tumor-treating field. In some aspects, the nanoparticles are nanoparticles that increase tissue permittivity. In some aspects, the target site is a stem cell target site. In some aspects, the altered electric impedance in the stem cell target site of the subject to the alternating current results in an increased mitotic effect of the alternating electric field in the stem cell target site.

In some aspects, a population of nanoparticles can be used in the methods disclosed herein. In some aspects, the population of nanoparticles can include conductive and non-conductive nanoparticles.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise combining the alternating electric fields are with an effective dose of an agent that targets dividing cells, which include without limitation alkylating agents, and the like.

Alkylating agents are known to act through the alkylation of macromolecules such as the DNA of cancer cells, and are usually strong electrophiles. This activity can disrupt DNA synthesis and cell division. Examples of alkylating reagents suitable for use herein include nitrogen mustards and their analogues and derivatives including, cyclophosphamide, ifosfamide, chlorambucil, estramustine, mechlorethamine hydrochloride, melphalan, and uracil mustard. Other examples of alkylating agents include alkyl sulfonates (e.g. busulfan), nitrosoureas (e.g. carmustine, lomustine, and streptozocin), triazenes (e.g. dacarbazine and temozolomide), ethylenimines/methylmelamines (e.g. altretamine and thiotepa), and methylhydrazine derivatives (e.g. procarbazine). Included in the alkylating agent group are the alkylating-like platinum-containing drugs comprising carboplatin, cisplatin, and oxaliplatin.

Additional agents can include, but are not limited to, analogues and derivatives of folic acid, pyrimidines, purines, and cytidine. Members of the folic acid group of agents suitable for use herein include, but are not limited to, methotrexate (amethopterin), pemetrexed and their analogues and derivatives. Pyrimidine agents suitable for use herein include, but are not limited to, cytarabine, floxuridine, fluorouracil (5-fluorouracil), capecitabine, gemcitabine, and their analogues and derivatives. Purine agents suitable for use herein include, but are not limited to, mercaptopurine (6-mercaptopurine), pentostatin, thioguanine, cladribine, and their analogues and derivatives. Cytidine agents suitable for use herein include, but are not limited to, cytarabine (cytosine arabinodside), azacitidine (5-azacytidine) and their analogues and derivatives.

Antimitotic agents suitable for use herein include, but are not limited to, vinca alkaloids like vinblastine, vincristine, vindesine, vinorelbine, and their analogues and derivatives, and podophyllotoxins, which include, but are not limited to etoposide, teniposide, and their analogues and derivatives. Antineoplastic agents suitable for use herein include, but are not limited to, belomycin, dactinomycin, doxorubicin, idarubicin, epirubicin, mitomycin, mitoxantrone, pentostatin, plicamycin, and their analogues and derivatives. Camptothecin analogues and derivatives which are suitable for use herein and include camptothecin, topotecan, and irinotecan.

L. ALTERNATING ELECTRIC FIELDS

Figure 6:
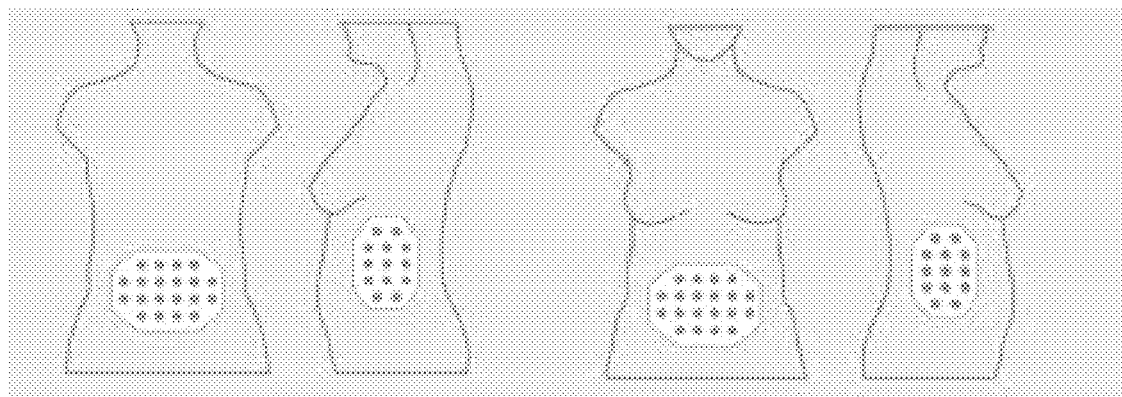
FIG. 6 shows a diagram of possible proposed placements of arrays on the front/back and sides of a patient that can be used with the systems and methods disclosed herein.
Figure 8:
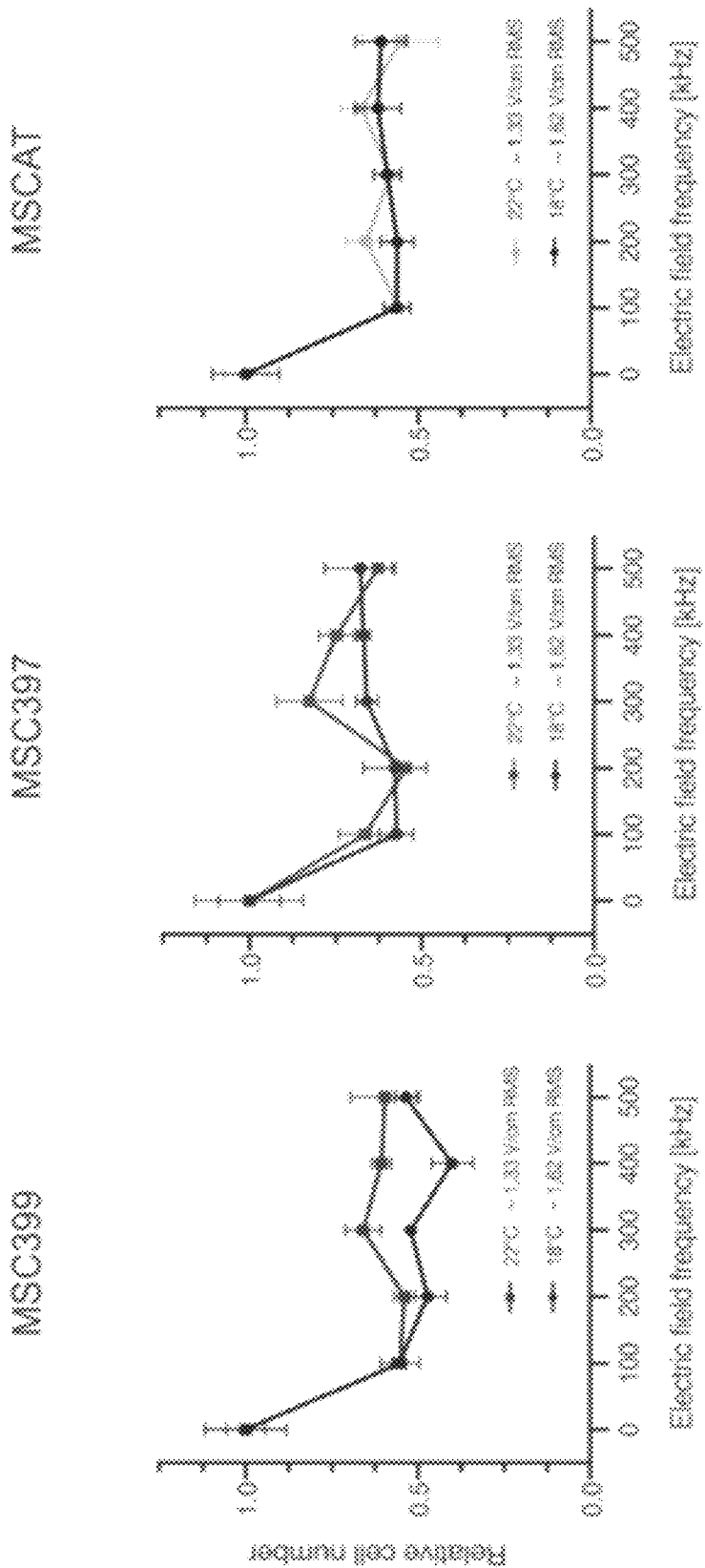
FIG. 8 shows the relative cell number vs the electric field frequency (kHz) for MSC399, MSC397 and MSCAT cells at 18° C. and 22° C.
Figure 9:
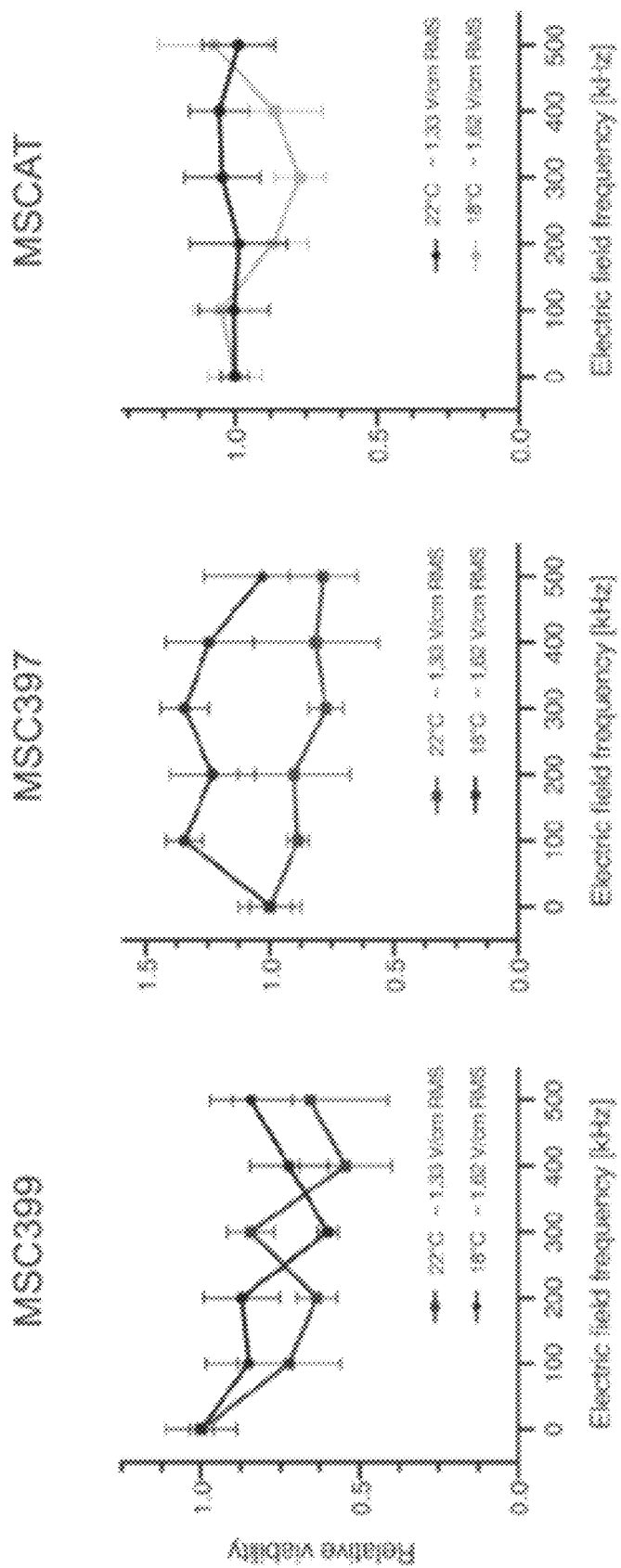
FIG. 9 shows the relative viability vs the electric field frequency (kHz) for MSC399, MSC397 and MSCAT cells at 18° C. and 22° C.

The methods disclosed herein utilize alternating electric fields. In some aspects, the alternating electric field used in the methods disclosed herein is a tumor-treating field. In some aspects, the alternating electric field (e.g. tumor-treating field) can vary dependent on the type of cell or condition to which the alternating electric fields is applied. In some aspects, the TTFields can be applied through one or more electrodes placed on the subject's body. In some aspects there can be two or more pairs of electrodes. For example, FIG. 6 shows a diagram of possible proposed placements of arrays on the front/back and sides of a patient that can be used with the systems and methods disclosed herein. In some aspects where two pairs of electrodes are used, the TTFields can alternate between the pairs of electrodes. For example, as seen in FIG. 6, a first pair of electrodes can be placed on the front and back of the subject and a second pair of electrodes can be placed on either side of the subject, the TTFields can then be applied and can alternate between the front and back electrodes and then to the side to side electrodes.

In some aspects, the frequency of the alternating electric fields can be 200 kHz. The frequency of the alternating electric fields can also be, but is not limited to, about 200 kHz, between 50 and 500 kHz, between 100 and 500 kHz, between 25 kHz and 1 MHz, between 50 and 190 kHz, between 25 and 190 kHz, or between 210 and 400 kHz.

In some aspects, the field strength of the alternating electric fields can be between 1 and 4 V/cm RMS. In some aspects, different field strengths can be used (e.g., between 0.1 and 10 V/cm).

In some aspects, the alternating electric fields can be applied for a variety of different intervals ranging from 0.5 hours to 72 hours. In some aspects, a different duration can be used (e.g., between 0.5 hours and 14 days). In some aspects, application of the alternating electric fields can be repeated periodically. For example, the alternating electric fields can be applied every day for a two hour duration.

In some aspects, the frequency of the alternating electric fields can be electric fields at 50 kHz, 100 kHz, 200 kHz, 300 kHz, 400 kHz, 500 kHz, or any frequency between.

In some embodiments the frequency of the alternating electric field is from about 200 kHz to about 400 kHz, from about 250 kHz to about 350 kHz, and may be around 300 kHz. In some embodiments the field is at least 1 V/cm. In some embodiments, the field is between 1 and 4 V/m. In other embodiments combinations of field strengths are applied, for example combining two or more frequencies at the same time, and/or applying two or more frequencies at different times.

In some aspects, the exposure may last for at least 12 hours, at least 24 hours, at least 36 hours, at least 48 hours, or at least 72 hours or more.

In some aspects, the nanoparticles are nanoparticles that increase tissue or cell permittivity.

In some aspects, the altered electric impedance in the target site or stem cell target site of the subject to the alternating current results in an increased anti mitotic effect of the alternating electric field in the target site. For example, the increased anti mitotic effect can refer to interference with proper micro-tubule assembly during metaphase which can eventually destroy the cells (e.g. pluripotent stem cells) present in or at the target site during telophase, cytokinesis, or subsequent interphase.

M. MULTIPLE FREQUENCIES

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise altering the electric impedance in a target site or stem cell target site with one frequency that allows nanoparticles to enter into pluripotent stem cells in the target site or stem cell target site and then applying a second frequency to the target site or stem cell target site wherein the electric impedance to the second frequency in the target site or stem cell target site is altered.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise altering the electric impedance in a target site or stem cell target site with one frequency (a first frequency) that allows nanoparticles to enter into pluripotent stem cells in the target site or stem cell target site and then applying a second frequency to the target site or stem cell target site wherein the electric impedance to the second frequency in the target site or stem cell target site is altered, further comprising applying multiple first and second frequencies. For example, the disclosed methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise altering the electric impedance to an alternating electric field in a target site or stem cell target site of a subject, comprising applying a first alternating electric field at a first frequency to the target site or stem cell target site for a first period of time, wherein application of the first alternating electric field at the first frequency to the target site or stem cell target site for the first period of time increases permeability of cell membranes of the pluripotent stem cells present in the target site or stem cell target site; introducing a nanoparticle to the target site or stem cell target site, wherein the increased permeability of the cell membranes enables the nanoparticle to cross the cell membranes; and applying a second alternating electric field at a second frequency to the target site or stem cell target site for a second period of time, wherein the second frequency is different from the first frequency, and wherein the impedance in the target site or stem cell target site of the subject of the second alternating electric field at the second frequency is altered. In some aspects, the current density and/or power loss density in the target site or stem cell target site of the subject to the alternating current is altered. In some aspects, the cells are pluripotent stem cells. In some aspects, the pluripotent stem cells are embryonic stem cells (ESCs), fetal stem cells (FSCs), or induced pluripotent stem cells (iPSCs). In some aspects, the step of introducing the nanoparticle begins at a given time, and wherein the step of applying the first alternating electric field ends at least 12 hours after the given time. In some aspects, the step of applying the first alternating electric field begins at least one hour before the given time. In some aspects, the second period of time comprises a plurality of non-contiguous intervals of time during which the second alternating electric field at the second frequency is applied to the pluripotent stem cells, wherein the plurality of non-contiguous intervals of time collectively add up to at least one week.

Also discussed herein are methods of using heat, or hyperthermia, to kill or ablate cells in a target site or pluripotent stem cell target site. For example, the methods disclosed herein can use one or more of the nanoparticles disclosed herein, wherein the nanoparticles are introduced into a cell in a target site or stem cell target site, and then exposed to an alternating electric field or alternating magnetic field (AMF). Exposure of the cells in the target site or stem cell target site to the alternating electric field or magnetic field (AMF) can cause the nanoparticles to heat (e.g. hit temperatures exceeding 100 degrees Fahrenheit), which can result in the killing the cells in the target site or stem cell target site.

Disclosed are methods of killing or ablating cells in a target site or stem cell target site with one frequency that allows nanoparticles to enter into cells in the target site or stem cell target site and then applying an alternating electric field or alternating magnetic field to the target site or stem cell target site, wherein the nanoparticles convert the alternating electric field or alternating magnetic field into thermal energy, thereby killing or ablating the cells in the target site or stem cell target site. In some aspects, the methods disclosed herein ca further comprise applying multiple first and second frequencies.

For example, disclosed are methods of ablating or killing cells in a target site or stem cell target site of a subject, comprising applying a first alternating electric field at a first frequency to the target site or stem cell target site for a first period of time, wherein application of the first alternating electric field at the first frequency to the target site or stem cell target site for the first period of time increases permeability of cell membranes of the cells present in the target site or stem cell target site; introducing a nanoparticle to the target site or stem cell target site, wherein the increased permeability of the cell membranes enables the nanoparticle to cross the cell membranes; and applying a second alternating electric field at a second frequency or an alternating magnetic field to the target site or stem cell target site for a second period of time, wherein one or more cells present in the target site or stem cell target site are killed or ablated. In some aspects, the second alternating electric field is a tumor-treating field.

In any of the methods disclosed herein, a subject can be exposed to or a system can be applied to the subject wherein the system includes one or more controllable low energy HF (High Frequency) carrier signal generator circuits, one or more data processors for receiving control information, one or more amplitude modulation control generators and one or more amplitude modulation frequency control generators. In some aspects, the amplitude modulation frequency control generators are adapted to accurately control the frequency of the amplitude modulations to within an accuracy of at least 1000 ppm, most preferably to within about 1 ppm, relative to one or more determined or predetermined reference amplitude modulation frequencies. Additional embodiments and specific frequencies for particular cancers are described in U.S. Pat. No. 8,977,365, which is hereby incorporated by reference in its entirety for it teaching of systems and methods useful for influencing cellular functions or malfunctions in a subject.

N. INCREASING ACTIVITY OF TTF BY ALTERING ELECTRIC FIELD'S DISTRIBUTION UTILIZING NANOPARTICLES

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; introducing a conductive nanoparticle to a target site in the subject; applying an alternating electric field to the target site and the site adjacent to the target site of the subject, wherein the efficacy of the alternating electric field in the target site of the subject is increased.

The methods of methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; introducing a conductive nanoparticle to a target site in the subject; applying an alternating electric field to the target site and the site adjacent to the target site of the subject, wherein the efficacy of the alternating electric field in the target site of the subject is increased, wherein the magnitude of the current density of the alternating electric field is increased in the target site.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; introducing a conductive nanoparticle to a target site in the subject; applying an alternating electric field to the target site and the site adjacent to the target site of the subject, wherein the efficacy of the alternating electric field in the target site of the subject is increased, wherein the impedance in the target site is lowered.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; introducing a conductive nanoparticle to a target site in the subject; applying an alternating electric field to the target site and the site adjacent to the target site of the subject, wherein the efficacy of the alternating electric field in the target site of the subject is increased, wherein the conductivity in the target site is increased and/or wherein the impedance in the site adjacent to the target site is increased.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; introducing a conductive nanoparticle to a target site in the subject; applying an alternating electric field to the target site and the site adjacent to the target site of the subject, wherein the efficacy of the alternating electric field in the target site of the subject is increased, wherein the alternating electric field is a tumor-treating field.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; introducing a conductive nanoparticle to a target site in the subject; applying an alternating electric field to the target site and the site adjacent to the target site of the subject, wherein the efficacy of the alternating electric field in the target site of the subject is increased, wherein the target site is a tumor target site.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; introducing a conductive nanoparticle to a target site in the subject; applying an alternating electric field to the target site and the site adjacent to the target site of the subject, wherein the increased efficacy of the alternating electric field in the target site results in an increased anti-mitotic effect of the alternating electric field in the target site.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the efficacy of the alternating electric field in the target site of the subject is increased.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the efficacy of the alternating electric field in the target site of the subject is increased, wherein the nanoparticle is a non-conductive nanoparticle.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the efficacy of the alternating electric field in the target site of the subject is increased, wherein the impedance in the non-target site adjacent to the target site is increased and/or wherein the conductivity in the non-target site adjacent to the target site is decreased.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the efficacy of the alternating electric field in the target site of the subject is increased, wherein the impedance in the target site is lowered and/or wherein the conductivity in the target site is increased.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the efficacy of the alternating electric field in the target site of the subject is increased, wherein the magnitude of the current density of the alternating electric field is decreased in the non-target site adjacent to the target site.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the efficacy of the alternating electric field in the target site of the subject is increased, further comprising introducing a conductive nanoparticle to the target site in in the subject. In some aspects, the impedance in the target site is lowered.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the efficacy of the alternating electric field in the target site of the subject is increased, wherein the alternating electric field is a tumor-treating field.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the efficacy of the alternating electric field in the target site of the subject is increased, wherein the target site is a tumor target site. In some aspects, the increased efficacy of the alternating electric field in the target site results in an increased mitotic effect of the alternating electric field in the target site. In some aspects, the nanoparticle is introduced into pluripotent stem cells in the target site. In some aspects, the nanoparticle is introduced into the pluripotent stem cells via injection post primary tumor resection. In some aspects, the nanoparticle is introduced into the pluripotent stem cells via intracellular injection (e.g. computed tomography-guided, during surgery or biopsy).

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the nanoparticle is introduced at about 0.001 to 0.01, 0.01 to 0.1, 0.1 to 0.5, 0.5 to 5, 5 to 10, 10 to 20, 20 to 50, 50 to 100, 100 to 200, 200 to 300, 300 to 400, 400 to 500, 500 to 600, 600 to 700, 700 to 800, 800 to 900, or 900 to 1000 ng per mm$^3$ tumor.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the nanoparticle is introduced at about 0.001 to 0.01, 0.01 to 0.1, 0.1 to 0.5, 0.5 to 5, 5 to 10, 10 to 20, 20 to 50, 50 to 100, 100 to 200, 200 to 300, 300 to 400, 400 to 500, 500 to 600, 600 to 700, 700 to 800, 800 to 900, or 900 to 1000 µg.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the nanoparticle is introduced once, twice, three or more times.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the conductive nanoparticle comprises or consists of carbon gold, ferrous iron, selenium, silver, copper, platinum, iron oxide, graphene, iron dextran, superparamagnetic iron oxide, boron-doped detonation nanodiamonds, or a combination thereof. In some aspects, the conductive nanoparticle comprises an alloy selected from Au/Ag, Au/Cu, Au/Ag/Cu, Au/Pt, Au/Fe, Au/Cu or Au/Fe/Cu.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the size of the nanoparticle is between 0.5 nm and 100 nm.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the size of the nanoparticle is between 0.5 nm and 2.5 nm.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the size of the nanoparticle is greater than 100 nm.

The methods of preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy disclosed herein can further comprise increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the size of the nanoparticle is between 100 nm and 200 nm.

O. DEVICES

Disclosed are devices for effectively preventing or disrupting mitosis of pluripotent stem cells, killing pluripotent stem cells, preventing or disrupting division of pluripotent stem cells, reducing the viability of pluripotent stem cells, slowing the progression or differentiation of pluripotent stem cells, and treating an ectopic pregnancy. Disclosed are devices that include: a signal generator; a temperature sensor electrically connected to the signal generator; and a pair of electrodes which receive an AC voltage from the signal generator, wherein the signal generator is configured to generate an electric field between the pair of electrodes so as to change orientations of a nanoparticle inside a pluripotent stem cell, the temperature sensor measures a temperature around the pluripotent stem cell, and the signal generator is configured to change an intensity of the electric field on the basis of the measured temperature.

Disclosed are devices that include: a signal generator; a temperature sensor electrically connected to the signal generator; and a pair of electrodes which receive an AC voltage from the signal generator, wherein the signal generator is configured to generate an electric field between the pair of electrodes so as to change orientations of a nanoparticle adjacent to a pluripotent stem cell, the temperature sensor measures a temperature around the pluripotent stem cell, and the signal generator is configured to change an intensity of the electric field on the basis of the measured temperature.

In an embodiment, the electric field has a frequency of about 100 KHz to about 500 KHz.

In an embodiment, the nanoparticles are conductive nanoparticles. In an embodiment, the nanoparticles are nonconductive nanoparticles. In an embodiment, the nonconductive nanoparticles are ferroelectric nanoparticles. In an embodiment, the ferroelectric particles have diameters of greater than about 0 nm to ≤about 50 nm. In an embodiment, the ferroelectric particles comprise BaTiO3 or SrTiO3.

In an embodiment, the first electrode and the second electrode include ferroelectrics.

Disclosed are devices that comprise: a first electrode and a temperature sensor on one surface of a first patch; a second electrode and a temperature sensor on one surface of a second patch; and a signal generator electrically connected to the first electrode and the second electrode, wherein the signal generator is configured to generate an electric field between the first electrode and the second electrode so as to change orientations of nanoparticle probes in the pluripotent stem cell, each of the first and second temperature sensors measures a temperature around the pluripotent stem cell, the signal generator is configured to change the intensity of the electric field on the basis of the measured temperature, and division of the pluripotent stem cell is suppressed according to the changed orientations of the nanoparticles. In an embodiment, the nanoparticle probes comprises a nanoparticle, a plurality of biomarkers attached to the nanoparticle particle, wherein the biomarkers may target the pluripotent stem cell and a passivation film coated on the nanoparticle. In an embodiment, the nanoparticle probes can move inside the pluripotent stem cell by the electric field.

Disclosed are devices comprising: a signal generator; a first electrode and a second electrode which face each other; a third electrode and a fourth electrode which face each other; and a temperature sensor electrically connected to the signal generator, wherein the first electrode and the second electrode receive a first AC voltage from the signal generator, the third electrode and the fourth electrode receive a second AC voltage from the signal generator, the signal generator generates a first electric field between the first electrode and the second electrode so as to change the orientation of a nanoparticle inside a pluripotent stem cells, the signal generator generates a second electric field between the third electrode and the fourth electrode so as to change an orientation of polar molecules inside the cancer cell, and the first electric field and the second electric field have mutually different frequencies. In an embodiment, the nanoparticle is a conductive nanoparticle.

Disclosed are devices comprising: a signal generator; a first electrode and a second electrode which face each other; a third electrode and a fourth electrode which face each other; and a temperature sensor electrically connected to the signal generator, wherein the first electrode and the second electrode receive a first AC voltage from the signal generator, the third electrode and the fourth electrode receive a second AC voltage from the signal generator, the signal generator generates a first electric field between the first electrode and the second electrode so as to change the orientation of a nanoparticle inside a pluripotent stem cells, the signal generator generates a second electric field between the third electrode and the fourth electrode so as to change an orientation of polar molecules inside the cancer cell, and the first electric field and the second electric field have mutually different frequencies. In an embodiment, the nanoparticle is a nonconductive nanoparticle. In an embodiment, the nonconductive nanoparticles are ferroelectric nanoparticles. In an embodiment, the ferroelectric particles have diameters of greater than about 0 nm to ≤about 50 nm. In an embodiment, the ferroelectric particles comprise BaTiO3 or SrTiO3.

In some aspects, the TTFields can be applied through one or more electrodes placed on the subject's body. In some aspects there can be two or more pairs of electrodes. For example, FIG. 6 shows a diagram of possible proposed placements of arrays on the front/back and sides of a patient that can be used with the systems and methods disclosed herein. In some aspects where two pairs of electrodes are used, the TTFields can alternate between the pairs of electrodes. For example, as seen in FIG. 6, a first pair of electrodes can be placed on the front and back of the subject and a second pair of electrodes can be placed on either side of the subject, the TTFields can then be applied and can alternate between the front and back electrodes and then to the side to side electrodes.

P. KITS

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for imaging and/or treating. In some aspects, the kit can comprise one or more of the disclosed nanoparticles. The kits also can contain equipment for applying alternating electrical fields. Disclosed herein are kits comprising one or more of the nanoparticles described herein in and a device capable of administering an alternating electric field. For example, disclosed herein are kits comprising one or more of the nanoparticles described herein in and a TTFields device (e.g., Optune®, Novocure Ltd.).

Q. EXAMPLES

SEEDING OF CELLS ONTO COVERSLIPS. Human pluripotent stem cells (including human embryonic stem cells [ESCs] and human induced pluripotent stem cells [iPSCs]) were maintained in Essential 8 (E8) media supplemented with 10 04 ROCK Inhibitor Y-27632. ESCs (WA07 [H7] line) or iPSCs were seeded onto the center of a 22 mm diameter glass or plastic coverslip in 6-well plates. The coverslips had been coated with Matrigel diluted 1:200 in DMEM/F12 beforehand for at least one hour at 37° C. in a conventional tissue culture incubator (37° C., 95% air, 5% CO2). Once the cells adhered to the coverslip, a total of 2 mL of E8 media supplemented with 10 µM ROCK Inhibitor Y-27632 was added to each well. Media was changed on a daily basis for 1-2 days as the cells recovered prior to transfer of coverslips to the ceramic dishes of the Inovitro™ TTFields device (Novocure Inc., Haifa, Israel).

The procedure for seeding the human ESC- or iPSC-derived cardiomyocytes (ESC-CMs or iPSC-CMs) was similar to that of the pluripotent stem cells except that the recovery period after seeding lasted longer (~5 days) until apparent spontaneous beating was observed. The ESC-CMs and iPSC-CMs were also maintained in RPMI 1640 medium containing B27 supplement plus insulin. A single monolayer of beating cardiac cells was visualized on the coverslips before starting the tumor-treating fields experiment. Imaging of cells was performed using a Leica DM IL LED inverted fluorescent microscope (Leica Microsystems, Buffalo Grove, IL) or a Revolve microscope (Echo laboratories, San Diego, CA).

TRYPAN BLUE CELL-COUNTING ASSAY USING AN AUTOMATED CELL COUNTER. Coverslips in ceramic dishes were prepared for cell counting by removing the media in addition to two washes of 2 mL of PBS. The coverslips were then transferred to a 6-well plate, whereupon 0.5 mL of Trypsin-LE (TrypLE) was added. Detached cells were suspended in a 15 mL Falcon Tube containing either 4.5 mL of E8 media supplemented with 10 µM ROCK Inhibitor Y-27632 (for ESCs and iPSCs) The cells were centrifuged at 300 g for 5 minutes at room temperature. Once a pellet was obtained, the supernatant was aspirated and cells were resuspended in either 10 mL of Essential 8 for cell count.

A 10 µL aliquot was taken and placed into a 1.5 mL Eppendorf tube. 10 µL of 0.4% Trypan Blue solution was then added to the cell culture aliquot, mixed by pipetting up and down, and loaded into one of the wells of the cell-counting slide. Cells were counted using a LUNA-FL Dual Fluorescence automated cell counter (Logos Biosystems, Annandale, VA, USA). Total live and dead cell counts were calculated and averaged from 3 technical replicates for each experimental condition (e.g., control [no TTF], 50 kHz, 100 kHz, 200 kHz, 300 kHz, 400 kHz and 500 kHz). The total cell counts were extrapolated based on a 1:10 dilution factor from original cell suspension.

QUANTITATIVE MEASURE OF CELL VIABILITY USING THE CELLTITER-GLO 2.0 ASSAY. Cellular viability of the human pluripotent stem cells was quantitatively measured using the CellTiter-Glo 2.0 assay (Promega, Madison, WI, USA). The CellTiter-Glo 2.0 assay provides a homogeneous method to determine the number of viable cells in culture by quantitating the amount of ATP present, which indicates the presence of metabolically active cells. Mono-oxygenation of luciferin is catalyzed by luciferase in the presence of Mg2+, ATP (which is contributed by viable cells), and molecular oxygen. A volume of CellTiter-Glo 2.0 reagent equal to the volume of cell culture medium present in each well was added (e.g., 0.5 mL of CellTiter-Glo 2.0 reagent was added to 0.5 mL of medium containing cells). The contents were mixed for 2 minutes on an orbital shaker to induce cell lysis. The 6-well plate was allowed to incubate at room temperature for 10 minutes to stabilize the luminescent signal. Afterwards, 50 µl from each well was transferred in triplicates to a white 96-well plate. The luminescence was recorded on a Synergy HTX multi-mode plate reader (BioTek, Winooski, VT, USA) using a 1 sec integration time. The BioTek GenS 3.03 software was used to analyze the luminescence signal.

CONTRACTILITY ASSAY. Contractility measurements of the stem cell-derived cardiomyocytes were assessed by a Sony SI8000 Live Cell Imaging System (Sony Biotechnology, San Jose, CA) before and after applying the tumor treating fields. ESC-CMs or iPSC-CMs were treated at various alternating electric field frequencies (e.g., 50 kHz, 100 kHz, 200 kHz, 300 kHz, 400 kHz and 500 kHz) for 72 hours. The control dishes did not have any alternating electric field applied to them. Data was acquired using a high-performance video camera that utilized a unique motion vector software to capture the motion of cells with high temporal and spatial fidelity. Post-image acquisition, displacements and magnitudes of cellular motions were calculated using a motion detection algorithm developed by Sony Biotechnology. Regions of interest (ROIs) were positioned over single cells or clusters of cardiac cells and various contraction and relaxation parameters were calculated.

FLUORESCENCE-ACTIVATED CELL SORTING (FACS) AND CELL CYCLE ANALYSIS. For FACS and cell cycle analysis studies, we harvested the H7 ESCs after the specified alternating electric field experimental conditions, and washed them with PBS. We then fixed the cells in ice cold 70% ethanol for 2 h at −20° C. After fixation, we collected the cells by centrifugation and stained them with 1.0 mL of PBS containing 10 µg/mL propidium iodide (PI), 100 µg/mL RNase A, and 0.05% Triton X-100. The cells were incubated in PI solution for 15 min at room temperature in the dark and washed once with PBS, re-suspended in 0.5 ml PBS, and assessed for live and dead cells using the InCyte software in a Guava FACS analyzer (EMD Millipore, Burlington, MA), and for cell cycle status using the Guava cell cycle analysis software. We analyzed the results using FlowJo software (Tree Star, Ashland, OR) for measuring live/dead cells and cell cycle status.

CULTURE AND MAINTENANCE OF HUMAN PLURIPOTENT STEM CELLS (hESCs and hiPSCs) GENERATION OF iPSCs. Dermal fibroblasts from a healthy human donor were reprogrammed into iPSCs using non-integrating Sendai virus vectors carrying the following transcription factors: Oct4, Sox2, Nanog, and cMyc.

ESC CULTURE AND MAINTENANCE. The human ESC line used in these experiments was the WA07 (H7) line transfected with a lentivirus vector that expresses Luciferase and Tomato Red under the EF1a promoter. The ESCs were grown to 90% confluence on Matrigel coated plates (ES Qualified, BD Biosciences, San Diego, CA) using a chemically defined E8 medium as previously described. The medium was changed on a daily basis, and cells were passaged every 3-4 days with EDTA (Thermo Fisher Scientific, CA). 10 µM ROCK Inhibitor Y-27632 was supplemented to dissociated cells prior to plating to prevent apoptosis.

CELL INJECTIONS IN MICE. Female immunodeficient nude (NU/NU) mice were anesthetized with 2% isoflurane and subcutaneously injected with approximately 500,000 H7 ESCs. The H7 ESCs were suspended in 100 µL Matrigel before being injected into the right flanks of the mice using a 28-gauge syringe needle. Moreover, the alternating electric field-treated H7 ESCs (i.e., those treated at 300 kHz for 3-4 days) were subcutaneously injected in the left flanks of the mice. A Matrigel only injection in the left shoulder blade was used as our control. Syringes were kept on ice prior to injection to prevent solidification of Matrigel at room temperature. The Stanford Administrative Panel on Laboratory Animal Care (APLAC) approved all animal procedures.

BIOLUMINESCENCE IMAGING (BLI) OF TRANSPLANTED CELLS TO ASSESS CELL SURVIVAL AND TERATOMA FORMATION. BLI was performed to track cell proliferation during the course of this study. In-vivo BLI was performed on the IVIS Spectrum imaging system (Xenogen Corporation, Alameda, CA) for up to 5-weeks post-cell injection. Cell survival and proliferation were monitored at day 0, 1, 3, 7, and every 7 days for up to 35 days post-cell transplantation. 1 gram of D-Luciferin Firefly potassium salt was diluted in 23 mL PBS, and 300 µl of this mixture was administered intraperitoneally using a 28-gauge insulin syringe needle. Ten minutes after intraperitoneal injection, animals were imaged for 20 minutes using 1 second to 5 min acquisition windows. Living Image software (Caliper LifeSciences, version 4.3.1) was used to analyze the bioluminescent images at different time points. ROIs were drawn over the sites of cell injection and the control region. The luminescence signal was quantified in radiance units of photons per second per square centimeter per steradian (photons/sec/cm2/sr).

TERATOMA EXPLANTATION AND HISTOLOGY. After the teratoma grew to a size of about 15 mm in diameter, the mice were euthanized and the teratomas were excised, fixed with 4% paraformaldyhyde, and sent to a pathological core lab for paraffin sectioning and H&E staining STATISTICAL ANALYSIS. Statistical analysis was performed using GraphPad Prism (version 7.04) and SPSS (IBM, version 21). Tests that had an alpha level for significance set at P<0.05 were considered significant. Data are reported as mean±standard deviation unless otherwise noted.

Those skilled in the art will recognize, or be able to ascertain using no more than routine experimentation, many equivalents to the specific embodiments of the method and compositions described herein. Such equivalents are intended to be encompassed by the following claims.

I claim:
1. A method of treating ectopic pregnancy comprising:
a. applying an alternating electric field to a target site of the subject for a period of time, the alternating electric field having a frequency and field strength,
wherein the target site comprises an ectopic pregnancy,
b. introducing a nanoparticle to the target site in the subject; and
c. applying an alternating electric field to the target site of the subject,
wherein the electric impedance in the target site of the subject to the alternating electric field is altered.

2. The method of claim 1, wherein the current density and/or power loss density in the target site of the subject to the alternating current is altered.

3. The method of claim 1, wherein the nanoparticle is a conductive nanoparticle.

4. The method of claim 3, wherein the impedance in the target site is lowered.

5. The method of claim 3, wherein the conductivity in the target site is increased.

6. The method of claim 1, wherein the nanoparticle is a non-conductive nanoparticle.

7. The method of claim 6, wherein the impedance in the target site is increased.

8. The method of claim 6, wherein the conductivity in the target site is decreased.

9. The method of claim 1, wherein the nanoparticle is introduced into a pluripotent stem cell in the target site.

10. The method of claim 1, wherein the frequency is 25 kHz to 1 MHz.

\* \* \* \* \*